United States Patent
Usuki

(10) Patent No.: US 9,556,119 B2
(45) Date of Patent: Jan. 31, 2017

(54) PROCESS FOR PREPARING DESMOSINE, ISODESMOSINE, AND DERIVATIVES THEREOF

(71) Applicant: SOPHIA SCHOOL CORPORATION, Tokyo (JP)

(72) Inventor: Toyonobu Usuki, Tokyo (JP)

(73) Assignee: SOPHIA SCHOOL CORPORATION, Tokyo (JP)

( * ) Notice: Subject to any disclaimer, the term of this patent is extended or adjusted under 35 U.S.C. 154(b) by 0 days.

(21) Appl. No.: 14/765,068

(22) PCT Filed: Jan. 24, 2014

(86) PCT No.: PCT/JP2014/051482
§ 371 (c)(1),
(2) Date: Jul. 31, 2015

(87) PCT Pub. No.: WO2014/119479
PCT Pub. Date: Aug. 7, 2014

(65) Prior Publication Data
US 2015/0376127 A1     Dec. 31, 2015

(30) Foreign Application Priority Data
Feb. 1, 2013  (JP) ................................ 2013-018473

(51) Int. Cl.
*C07D 213/55*     (2006.01)

(52) U.S. Cl.
CPC .................... *C07D 213/55* (2013.01)

(58) Field of Classification Search
CPC ................................................. C07D 213/55
See application file for complete search history.

(56) References Cited

FOREIGN PATENT DOCUMENTS

| | | |
|---|---|---|
| CN | 1156990 A | 8/1997 |
| EP | 0 196 007 A2 | 10/1986 |
| WO | 96/00216 A1 | 1/1996 |
| WO | 2006/046626 A1 | 5/2006 |

OTHER PUBLICATIONS

Davis, J Am Chem Soc, 92:12, 3778-3782, 1970.*
Akagawa, Connective Tissue Research, vol. 41(2), 131-141, 2000.*
Toyonobu Usuki, et al., "Total synthesis of COPD biomarker desmosine that crosslinks elastin", Chem. Commun., 2012, pp. 3233-3235, vol. 48.
Hiroto Yanuma, et al., "Total synthesis of the COPD biomarker desmosine via Sonogashira and Negishi cross-coupling reactions", Tetrahedron Letters, 2012, pp. 5920-5923, vol. 53.
Li-Bing Yu, et al., "Lanthanide-Promoted Reactions of Aldehydes and Amine Hydrochlorides in Aqueous Solution. Synthesis of 2,3-Dihydropyridinium and Pyridinium Derivatives", J. Org. Chem., 1997, pp. 208-211, vol. 62.
Yohei Koseki, et al., "Efficient synthesis of benzyl 2-(S) -[(tert-butoxycarbonyl)amino]—ω—iodoalkanoates", Tetrahedron: Asymmetry, 2011, pp. 580-586, vol. 22.
Mitsugu Akagawa, et al, "Mechanism of Formation of Elastin Crosslinks", Connective Tissue Research, 2000, pp. 131-141, vol. 41, No. 2.
Norman R. Davis, et al, "On the Mechanism of Formation of Desmosine and Isodesmosine Cross-Links of Elastin", Journal of the American Chemical Society, Jun. 17, 1970, pp. 3778-3782, vol. 92, No. 12.
Takeo Nakanishi, et al., "Formation of Phosphatidyl 1-(2-Hydroxyethyl)-2,3,5-Trialkyl Pyridinium on Heating Phosphatidyl Ethanolamine with n-Alkanal", Agricultural and Biological Chemistry, 1974, pp. 1141-1147, vol. 38, No. 6.
International Search Report for PCT/JP2014/051482 dated Feb. 18, 2014 [PCT/ISA/210].
Communication dated Sep. 2, 2016, from the State Intellectual Property Office of the P.R.C. in counterpart Chinese application No. 201480007160.7.

* cited by examiner

*Primary Examiner* — D Margaret M. Seaman
(74) *Attorney, Agent, or Firm* — Sughrue Mion, PLLC

(57) ABSTRACT

A process for preparing a compound represented by the following general formula (I) or a salt thereof, which comprises reacting lysine or a protective product thereof or a salt thereof with allysine or a protective product thereof in the presence of a specific trifluoromethane sulfonate to obtain a compound having pyridine ring or a salt thereof.

[Chem. (1)]

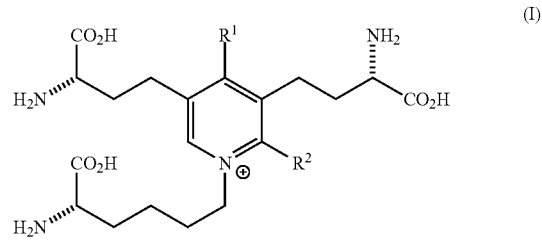

(I)

(wherein, in the above-described general formula (I), one of $R^1$ and $R^2$ is $-CH_2CH_2CH_2CH(NH_2)COOH$ group, and the other is hydrogen atom. And wherein, in the above-described general formula (I), one, or two or more of hydrogen atom, one, or two or more of carbon atom, or one, or two or more of nitrogen atom may be substituted with their isotope.)

8 Claims, No Drawings

PROCESS FOR PREPARING DESMOSINE, ISODESMOSINE, AND DERIVATIVES THEREOF

CROSS REFERENCE TO RELATED APPLICATIONS

This application is a National Stage of International Application No. PCT/JP2014/051482, filed on Jan. 24, 2014, which claims priority from Japanese Patent Application No. 2013-018473, filed on Feb. 1, 2013, the contents of all of which are incorporated herein by reference in their entirety.

TECHNICAL FIELD

The present invention relates to a process for preparing desmosine, isodesmosine and derivatives thereof, and analogs thereof.

BACKGROUND ART

Chronic Obstructive Pulmonary Disease (COPD) is a generic designation of diseases such as bronchitis and pulmonary emphysema. According to the World Health Organization (WHO), it ranks the fourth place of the cause of death, and it is warned that this will rank up to the third place by 2020. Concerning the COPD, a root pathological condition thereof is extremely complicated and contains large majority of unknown clinical states, and even radical therapeutic agent does not exist. In this century, it is feared to rapidly increase the number of the COPD patients on a global scale due to increased number of smokers and atmospheric pollutions caused by industrial developments in developing countries, and therefore an establishment of a rapid and simple detection method becomes an overarching imperative.

Hydrolytic processing of sputum, blood, urine of a COPD patient is conducted and the obtained samples are analyzed with Liquid Chromatography-Mass Spectrometry (LC-MS) to provide observations of desmosine, which serves as a crosslinking amino acid of an elastic fiber elastin controlling an expansion and a contraction of a lung alveolus and is represented by the following formula (1), and isodesmosine, which is an isomer thereof and is shown in the following formula (2). Desmosines are expected as promising biomarkers for COPD, since the quantity thereof existing in a COPD patient is distinctive as compared with that of a healthy person.

[Chem. (1)]

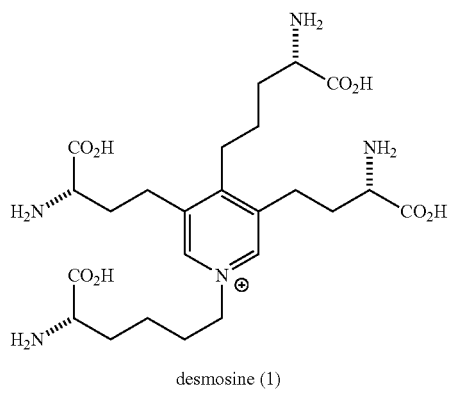

desmosine (1)

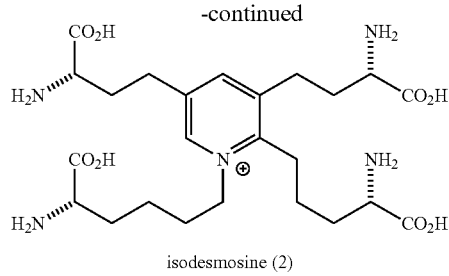

isodesmosine (2)

Technologies related to a total synthesis of desmosine are described in Non-Patent Documents 1 and 2.

Although a technical field is different, technology related to a synthetic process of compounds having pyridine ring is described in Non-Patent Document 3.

RELATED DOCUMENTS

Non-Patent Documents

[Non-Patent Document 1]

Toyonobu Usuki, and other 7 authors, "Total synthesis of COPD biomarker desmosine that crosslinks elastin", Chem. Commun., 2012, Vol. 48, pp. 3233 to 3235.

[Non-Patent Document 2]

Hiroto Yanuma, and another author, "Total synthesis of the COPD biomarker desmosine via Sonogashira and Negishi cross-coupling reactions", Tetrahedron Lett., 2012, Vol. 53, pp. 5920 to 5922.

[Non-Patent Document 3]

Li-Bing Yu and other 4 authors, "Lanthanide-Promoted Reactions of Aldehydes and Amine Hydrochlorides in Aqueous Solution. Synthesis of 2,3-Dihydropyridinium and Pyridinium Derivatives", J. Org. Chem., 1997, Vol. 62, pp. 208 to 211.

[Non-Patent Document 4]

Yohei Koseki and other 2 authors, "Efficient synthesis of benzyl 2-(S)-[(tert-butoxycarbonyl)amino]-ω-iodoalkanoates", Tetrahedron: Asymmetry, 2011, Vol. 22, pp. 580 to 586.

SUMMARY OF THE INVENTION

Problems to be Solved by the Invention

The present invention is to provide a novel process for stably preparing desmosine, isodesmosine or derivatives thereof with reduced number of process steps.

Means for Solving the Problems

According to one aspect of the present invention, there is provided a process for preparing a compound presented by the following general formula (I) or a salt thereof,

[Chem. (2)]

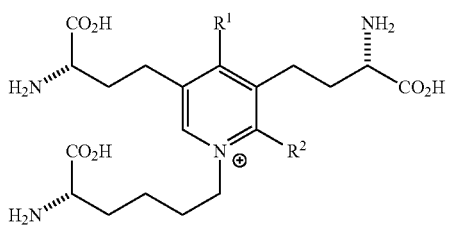

(I)

(Wherein, in the above-described general formula (I), one of $R^1$ and $R^2$ is —$CH_2CH_2CH_2CH(NH_2)COOH$ group, and the other is hydrogen atom. And wherein, in the above-described general formula (I), one, or two or more of hydrogen atom, one, or two or more of carbon atom, or one, or two or more of nitrogen atom may be substituted with their isotope.) the process comprising:

reacting a compound represented by the following general formula (XII) or a salt thereof with a compound represented by the following general formula (XIII) in the presence of a compound represented by the following general formula (XIV), to create a compound represented by the following general formula (XV) or a salt thereof.

[Chem. (3)]

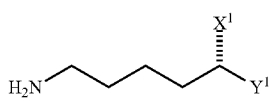

(XII)

(Wherein, in the above-described general formula (XII), $X^1$ is an amino group that may be protected, and $Y^1$ is a carboxylic group that may be protected. And wherein, in the above-described general formula (XII), one, or two or more of hydrogen atom, one, or two or more of carbon atom, or one, or two or more of nitrogen atom may be substituted with their isotope.)

[Chem. (4)]

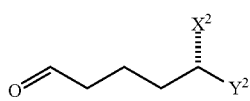

(XIII)

(Wherein, in the above-described general formula (XIII), $X^2$ is an amino group that may be protected, and $Y^2$ is a carboxylic group that may be protected. And wherein, in also the above-described general formula (XIII), one, or two or more of hydrogen atom, one, or two or more of carbon atom, or one, or two or more of nitrogen atom may be substituted with their isotope.)

$M(OTf)_3$ (XIV)

(Wherein, in the above-described general formula (XIV), M is a trivalent metallic atom, and Tf is trifluoromethyl sulphonyl group.)

[Chem. (5)]

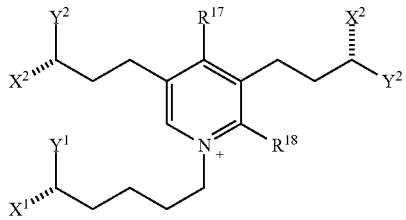

(XV)

(Wherein, in the above-described general formula (XV), $X^1$ and $Y^1$ are identical to $X^1$ and $Y^1$ in the general formula (XII), respectively, and $X^2$ and $Y^2$ are identical to $X^2$ and $Y^2$ in the general formula (XIII) respectively. And wherein one of $R^{17}$ and $R^{18}$ is a —$CH_2CH_2CH_2CHX^2Y^2$ group, and the other is hydrogen atom, and $X^2$ and $Y^2$ are identical to $X^2$ and $Y^2$ in the general formula (XIII), respectively. And wherein, in the above-described general formula (XV), one, or two or more of hydrogen atom, one, or two or more of carbon atom, or one, or two or more of nitrogen atom may be substituted with their isotope.)

According to another aspect of the present invention, there is provided a process for preparing a compound represented by the following general formula (I) or a salt thereof:

[Chem. (6)]

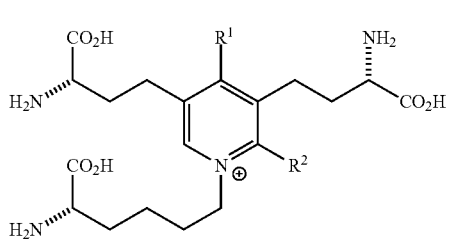

(I)

(Wherein, in the above-described general formula (I), one of $R^1$ and $R^2$ is —$CH_2CH_2CH_2CH(NH_2)COOH$ group, and the other is hydrogen atom. And wherein, in the above-described general formula (I), one, or two or more of hydrogen atom, one, or two or more of carbon atom, or one, or two or more of nitrogen atom may be substituted with their isotope.)

the process comprising:

reacting a compound represented by the following general formula (II) or a salt thereof with a compound represented by the following general formula (III) in the presence of a lanthanoid compound represented by the following general formula (IV) to create a compound represented by the following general formula (V) or a salt thereof; and converting the compound represented by the general formula (V) or the salt thereof into the compound represented by the general formula (I) or a salt thereof.

[Chem. (7)]

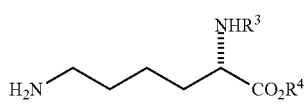

(II)

(Wherein, in the above-described general formula (II), $R^3$ is tert-butyloxycarbonyl group or benzyloxycarbonyl group, and $R^4$ is tert-butyl group, benzyl group, methyl group or ethyl group. And wherein, in the above-described general formula (II), one, or two or more of hydrogen atom, one, or two or more of carbon atom, or one, or two or more of nitrogen atom may be substituted with their isotope.)

[Chem. (8)]

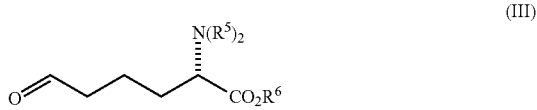
(III)

(Wherein, in the above-described general formula (III), each of $R^5$ is independently tert-butyloxycarbonyl group or benzyloxycarbonyl group, and $R^6$ is tert-butyl group, benzyl group, methyl group or ethyl group. And wherein, in the above-described general formula (III), one, or two or more of hydrogen atom, one, or two or more of carbon atom, or one, or two or more of nitrogen atom may be substituted with their isotope.)

$Ln(OTf)_3$ (IV)

(Wherein, in the above-described general formula (IV), Ln is La (lanthanum), Pr (praseodymium), Nd (neodymium), Gd (gadolinium), Sc (scandium), Y (yttrium), Dy (dysprosium), Er (erbium) or Yb (ytterbium), and Tf is trifluoromethyl sulphonyl group.)

[Chem. (9)]

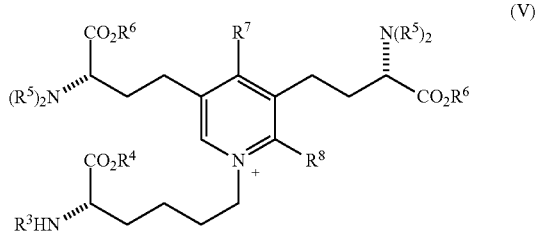
(V)

(Wherein, in the above-described general formula (V), $R^3$ and $R^4$ are identical to $R^3$ and $R^4$ in the general formula (II), respectively, and $R^5$ and $R^6$ are identical to $R^5$ and $R^6$ in the general formula (III), respectively. And wherein, one of $R^7$ and $R^8$ is a —$CH_2CH_2CH_2CH(N(R^5)_2)COOR^6$ group and the other is hydrogen atom, and, $R^5$ and $R^6$ are identical to $R^5$ and $R^6$ in the general formula (III), respectively. And wherein, in the above-described general formula (V), one, or two or more of hydrogen atom, one, or two or more of carbon atom, or one, or two or more of nitrogen atom may be substituted with their isotope.)

Advantageous Effects of Invention

According to the present invention, desmosine, isodesmosine or derivatives thereof, or analogs thereof, can be stably obtained in reduced number of process steps.

DESCRIPTION OF EMBODIMENTS

Embodiments of the present invention will be described below, in reference with specific examples. It would be understood that a combination of specific forms described in a plurality of embodiments may be employed.

First Embodiment

The present embodiment relates to a process for preparing a compound represented by the following general formula (I). The preparation process in the present embodiment includes the following process steps.
(Process Step 21): a process step for reacting a compound represented by the following general formula (XII) or a salt thereof with a compound represented by the following general formula (XIII) in the presence of a compound represented by the following general formula (XIV), to create a compound represented by the following general formula (XV) or a salt thereof.

[Chem. (10)]

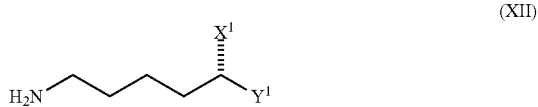
(XII)

(Wherein, in the above-described general formula (XII), $X^1$ is an amino group that may be protected, and $Y^1$ is a carboxylic group that may be protected. And wherein, in the above-described general formula (XII), one, or two or more of hydrogen atom, one, or two or more of carbon atom, or one, or two or more of nitrogen atom may be substituted with their isotope.)

[Chem. (11)]

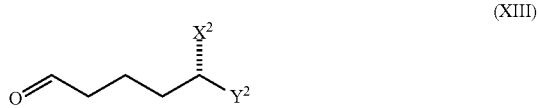
(XIII)

(Wherein, in the above-described general formula (XIII), $X^2$ is an amino group that may be protected, and $Y^2$ is a carboxylic group that may be protected. And wherein, in also the above-described general formula (XIII), one, or two or more of hydrogen atom, one, or two or more of carbon atom, or one, or two or more of nitrogen atom may be substituted with their isotope.)

$M(OTf)_3$ (XIV)

(Wherein, in the above-described general formula (XIV), M is a trivalent metallic atom, and Tf is trifluoromethyl sulphonyl group.)

[Chem. (12)]

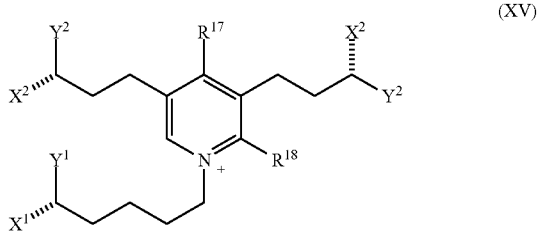
(XV)

(Wherein, in the above-described general formula (XV), $X^1$ and $Y^1$ are identical to $X^1$ and $Y^1$ in the general formula (XII), respectively, and $X^2$ and $Y^2$ are identical to $X^2$ and $Y^2$ in the general formula (XIII) respectively. And wherein one of $R^{17}$ and $R^{18}$ is a —$CH_2CH_2CH_2CHX^2Y^2$ group, and the other is hydrogen atom, and $X^2$ and $Y^2$ are identical to $X^2$ and $Y^2$ in the general formula (XIII), respectively. And wherein, in the above-described general formula (XV), one, or two or more of hydrogen atom, one, or two or more of carbon atom, or one, or two or more of nitrogen atom may be substituted with their isotope.)

[Chem. (13)]

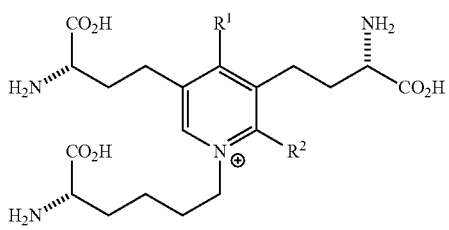

(I)

(Wherein, in the above-described general formula (I), one of $R^1$ and $R^2$ is —$CH_2CH_2CH_2CH(NH_2)COOH$ group, and the other is hydrogen atom. And wherein, in the above-described general formula (I), one, or two or more of hydrogen atom, one, or two or more of carbon atom, or one, or two or more of nitrogen atom may be substituted with their isotope.)

In the process step 21, lysine, which is a compound having amino group, or a protective product thereof or a salt thereof, and allysine, which is a compound having aldehyde group, or a protective product thereof, are employed as raw materials in Chichibabin pyridine synthesis with a catalyst of a metallic salt of trifluoromethane sulfonic acid to create pyridine ring, thereby obtaining a compound represented by general formula (XV) or a salt thereof.

Among the above-described raw materials, a compound represented by the general formula (XII) or a salt thereof is employed as a compound having amino group. In the general formula (XII), $X^1$ is an amino group that may be protected, and $Y^1$ is a carboxylic group that may be protected. Specific examples of the protective group in the case that $X^1$ is a protected amino group, and specific examples of the protective group in the case that $Y^1$ is a protected carboxylic group, will be described in the second embodiment, respectively.

Also, specific examples of salts of the compound represented by the general formula (XII) include a hydrochloride, a trifluoromethane sulfonate, and the like of a terminal amine in the general formula (XII). The uses of these salts can enhance, for example, a water solubility.

Also, a compound represented by the general formula (XIII) is employed as a compound having aldehyde group. In general formula (XIII), $X^2$ is an amino group that may be protected, and $Y^2$ is a carboxylic group that may be protected. Specific examples of the protective groups in the case that $X^2$ is a protected amino group, and specific examples of the protective groups in the case that $Y^2$ is a protected carboxylic group, will be described in the second embodiment, respectively.

The using amount of the compound represented by the general formula (XIII) in the process step 21 is not particularly limited so far as it does not inhibit the target reaction, and may be, for example, equal to or larger than 1 molar equivalent with respect to the compound represented by the general formula (XII), and preferably equal to or larger than 3 molar equivalents, and for example, equal to or lower than 20 molar equivalents, and preferably equal to or lower than 10 molar equivalents.

In addition, the compound represented by the general formula (XIII) may be synthesized through the known method. Specific examples of the synthesis will be described below in Examples.

The compound represented by the general formula (XIV) is a metallic salt of trifluoromethane sulfonic acid, and serves as a catalyst of the Chichibabin pyridine synthesis reaction. Also, the compound represented by the general formula (XIV) functions as a stable Lewis acid in, for example, a protic solvent. In the general formula (XIV), M represents trivalent metallic atom. Specific examples of M include lanthanides and transition metals. Specific examples of lanthanides include La (lanthanum), Pr (praseodymium), Nd (neodymium), Gd (gadolinium), Sc (scandium), Y (yttrium), Dy (dysprosium), Er (erbium), Yb (ytterbium), Sm (samarium), Eu (europium), Tb (terbium), Ho (holmium), Tm (thulium) and Lu (lutetium), and more specifically, compounds described in Second Embodiment may be employed. On the other hand, specific examples of transition metals include Cu (copper), Fe (iron) and Zn (zinc).

The type of the solvent used for the reaction is not particularly limited so far as it is stable under the reactive conditions and does not inhibit the target reaction, and may be, for example, one, two or more selected from water; alcohols such as ethanol, methanol and the like; and polar aprotic solvents such as acetone, dimethyl formamide, dimethyl sulfoxide and the like; and other organic solvents.

Among these, for example, water is employed as the reaction solvent, in view of providing improved operability in the preparation process.

Alternatively, a mixed solvent of, for example, water and alcohol, may be employed, and more specifically a mixed solvent of water and methanol may be employed.

The using amount of the solvent may be, for example, about 0.001 to 1 fold by mass with respect to the compound represented by the general formula (XII), and may be preferably 0.01 to 0.02 fold by mass.

The reaction temperature may be set as, for example, ranging from about −20 degrees Celsius (degrees C.) to the boiling point of the solvent, and may be equal to or higher than 20 degrees C., in view of the reaction kinetics. On the other hand, the reaction temperature may also be equal to or lower than 100 degrees C. in view of the stability of the reaction product.

Also, the reaction time can be determined according to the reaction temperature, a stirring efficiency and the like, and may be, for example, determined as ranging from 12 to 24 hours.

Also, the use of water as the reaction solvent in the process step 21 allows the selective synthesis between desmosine or derivatives thereof and isodesmosine or derivatives thereof.

More specifically, isodesmosine or derivatives thereof can be selectively obtained by selecting water as the reaction solvent, and selecting the reaction temperature to be equal to or higher than 70 degrees C., preferably equal to or higher than 75 degrees C., and on the other hand equal to or lower than 100 degrees C.

On the other hand, both desmosine or derivatives thereof and isodesmosine or derivatives thereof can be obtained in the same process step by selecting water as the reaction solvent, and selecting the reaction temperature to be equal to or higher than 0 degree C., and preferably equal to or higher than preferably 15 degrees C., and on the other hand, equal to or lower than 60 degrees C., and preferably equal to or lower than 40 degrees C.

When water is selected as the reaction solvent, the using amount of the solvent may be, for example, about 0.001 to 1 fold by mass with respect to the compound represented by the general formula (XII), and preferably 0.01 to 0.02 fold by mass.

Also, the reaction temperature may be set as, for example, ranging from about −20 degrees C. to the boiling point of the solvent, and may be preferably equal to or higher than 20 degrees C., in view of the reaction kinetics. On the other hand, the reaction temperature may also be equal to or lower than 100 degrees C. in view of the stability of the reaction product. Also, it is preferable to be equal to or lower than 0 degree C.

Also, the reaction time can be determined according to the reaction temperature, a stirring efficiency and the like, and may be, for example, determined as ranging from 12 to 24 hours.

When $X^1$, $Y^1$ in the general formula (XII) and $X^2$ and $Y^2$ in the general formula (XIII) are all unprotected amino groups or carboxyl groups, the compound represented by the general formula (XV) obtained in the process step (21) corresponds to the compound of formula (I), in other words, desmosine or isodesmosine.

On the contrary, when at least one of X, $Y^1$ in the general formula (XII) and $X^2$ and $Y^2$ in the general formula (XIII) is protected group, the following process step may be further included after the process step 21:

(Process Step 22) a process step for converting the compound represented by the general formula (XV) or a salt thereof into the compound represented by the general formula (I) or a salt thereof.

In the process step 22, the compound represented by the general formula (I) is obtained by deprotecting carboxyl group and amino group in the compound of the general formula (XV) obtained in the process step 21.

The deprotection method in the process step 22 will be further specifically described in Second Embodiment.

When $X^1$, $Y^1$ in the general formula (XII) and $X^2$ and $Y^2$ in the general formula (XIII) are protected amino group or carboxyl group, it is preferable in view of shortening the process step in the process step 22 that the same group is assigned for both $X^1$ of the general formula (XII) and $X^2$ of the general formula (XIII) and the same group is assigned for both $Y^1$ of the general formula (XII) and $Y^2$ of the general formula (XIII). Also, it is further preferably configured that $X^1$, $Y^1$, $X^2$ and $Y^2$ are groups that are removable in the same process step. This allows deprotecting $X^1$, $Y^1$, $X^2$ and $Y^2$ in a single step in the process step 22.

According to the present embodiment, the amino acid represented by the general formula (XII) or derivatives thereof and the amino acid aldehyde represented by the formula (XIII) are employed as the raw materials, and Chichibabin pyridine synthesis with metallic salt of trifluoromethane sulfonic acid represented by the general formula (XIV) serving as the catalyst is adopted as the key reaction, so that desmosine, isodesmosine and derivatives thereof can be obtained with reduced number of process steps and improved yield. This also allows stable creation of pyridine ring and suitable control of the location of the biding site of side-chain in pyridine ring.

In the following embodiment, the description will be made mainly in reference to the case that $X^1$, $Y^1$ in general formula (XII) and $X^2$ and $Y^2$ in the general formula (XIII) are protected amino groups or carboxyl groups.

Also, in the following embodiment, the description will be made mainly in reference to the case that lanthanoid salt is employed as a metallic salt of trifluoromethane sulfonic acid represented by the general formula (XIV).

Second Embodiment

The present embodiment relates to a process for preparing a compound represented by the following general formula (I). The preparation process in the present embodiment includes the following process steps.

(Process step 11) a process step of reacting a compound represented by the following general formula (II) or a salt thereof with a compound represented by the following general formula (III) in the presence of a lanthanoid compound represented by the following general formula (IV) to create a compound represented by the following general formula (V) or a salt thereof; and (Process Step 12) a process step for converting the compound represented by the general formula (V) or a salt thereof into the compound represented by the general formula (I) or a salt thereof.

[Cham. (14)]

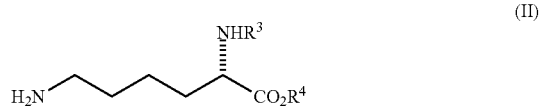

(Wherein, in the above-described general formula (II), $R^3$ is tert-butyloxycarbonyl group (hereinafter referred to as "Boc group".) or benzyloxycarbonyl group (hereinafter referred to as "Cbz group".), and $R^4$ is tert-butyl group (hereinafter referred to as "$^t$Bu group".), benzyl group (hereinafter referred to as "Bn group".), methyl group or ethyl group. And wherein, in the above-described general formula (II), one, or two or more of hydrogen atom, one, or two or more of carbon atom, or one, or two or more of nitrogen atom may be substituted with their isotope.)

[Cham. (15)]

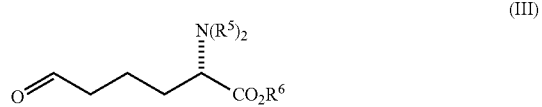

(Wherein, in the above-described general formula (III), each of $R^5$ is independently Boc group or Cbz group, and $R^6$ is $^t$Bu group, Bn group, methyl group or ethyl group. And wherein, in the above-described general formula (III), one, or two or more of hydrogen atom, one, or two or more of carbon atom, or one, or two or more of nitrogen atom may be substituted with their isotope.)

$$Ln(OTf)_3 \qquad (IV)$$

(Wherein, in the above-described general formula (IV), Ln is La, Pr, Nd, Gd, Sc, Y, Dy, Er or Yb, and Tf is trifluoromethyl sulphonyl group.)

[Chem. (16)]

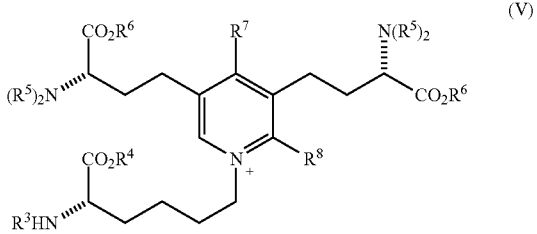

(Wherein, in the above-described general formula (V), $R^3$ and $R^4$ are identical to $R^3$ and $R^4$ in the general formula (II), respectively, and $R^5$ and $R^6$ are identical to $R^5$ and $R^6$ in the general formula (III), respectively. And wherein, one of $R^7$ and $R^8$ is a —$CH_2CH_2CH_2CH(N(R^5)_2)COOR^6$ group and the other is hydrogen atom, and, $R^5$ and $R^6$ are identical to $R^5$ and $R^6$ in the general formula (III), respectively. And wherein, in the above-described general formula (V), one, or two or more of hydrogen atom, one, or two or more of carbon atom, or one, or two or more of nitrogen atom may be substituted with their isotope.)

[Chem. (17)]

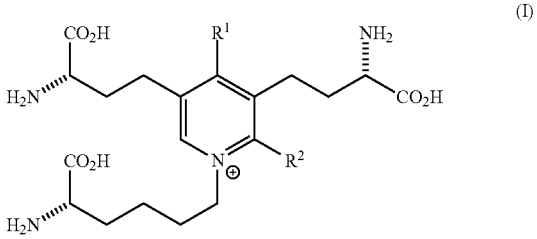

(Wherein, in the above-described general formula (I), one of $R^1$ and $R^2$ is —$CH_2CH_2CH_2CH(NH_2)COOH$ group, and the other is hydrogen atom. And wherein, in the above-described general formula (I), one, or two or more of hydrogen atom, one, or two or more of carbon atom, or one, or two or more of nitrogen atom may be substituted with their isotope.)

The compound, in which $R^1$ is —$CH_2CH_2CH_2CH(NH_2)COOH$ group and $R^2$ is hydrogen atom in the general formula (I), is desmosine represented by the formula (1). Also, the compound, in which $R^1$ is hydrogen atom and $R^2$ is —$CH_2CH_2CH_2CH(NH_2)COOH$ group, is isodesmosine represented by the formula (2).

More specific description will be made below in order of process step 11 and process step 12.

In the process step 11, a lysine protective product that is a compound having amino group or a salt thereof and an allysine protective product that is a compound having aldehyde group are employed as raw materials to create pyridine ring through Chichibabin pyridine synthesis with a catalyst of a lanthanoid compound, thereby obtaining the compound represented by the general formula (V) or a salt thereof.

Among the above-described raw materials, the compound represented by the general formula (II) or a salt thereof is employed as the compound having amino group. In the general formula (II), $R^3$ is Boc group or Cbz group, and preferably Boc group. Also, $R^4$ is $^tBu$ group, Bn group, methyl group or ethyl group, and preferably $^tBu$ group.

Specific examples of salts of the compound represented by the general formula (II) include hydrochloride, trifluoromethane sulfonate and the like of a terminal amine in the general formula (II). The use of these salts can enhance, for example, water solubility.

Also, the compound represented by the general formula (III) is employed as the compound having aldehyde group. In the general formula (III), $R^5$ is Boc group or Cbz group, and is preferably Boc group. While two of $R^5$ groups may be the same or may be different, these may preferably be of the same group, and more preferably both of $R^5$ groups are Boc group. $R^6$ is $^tBu$ group, Bn group, methyl group or ethyl group, and is preferably Bn group or $^tBu$ group.

Also, it is preferable in view of shortening the process step in the process step 12 as described later that the same group is assigned for $R^3$ in the general formula (II) and $R^5$ in the general formula (III), and the same group is assigned for $R^4$ in the general formula (II) and $R^6$ in the general formula (III). It is also preferable to be configured that $R^3$ to $R^6$ are the group that is removable in the same process step. More specifically, it is preferable to assign Boc group for both $R^3$ in the general formula (II) and $R^5$ in the general formula (III), and to assign $^tBu$ group for both $R^4$ in the general formula (II) and $R^6$ in the general formula (III). This allows deprotecting $R^3$ to $R^6$ in a single step in the process step 12.

The using amount of the compound represented by the general formula (III) is not particularly limited so far as it does not inhibit the target reaction, and may be, for example, equal to or larger than 3 molar equivalents and equal to or lower than 20 molar equivalents with respect to the compound represented by the general formula (II).

In addition, the compound represented by the general formula (III) may be synthesized by using known method. Specific examples of synthesis will be described below in Examples.

In the compound represented by the general formula (IV), Ln represents lanthanides and is specifically La, Pr, Nd, Gd, Sc, Y, Dy, Er or Yb. Preferable examples of Ln include Pr and La, and Pr is further preferable.

Alternatively, in place of Ln salt represented by the general formula (IV), a metallic salt described in First Embodiment or the like may be employed as trifluoromethane sulfonate.

The type of the solvent used for the reaction is not particularly limited so far as it is stable under the reactive conditions and does not inhibit the target reaction, and may be, for example, one, two or more selected from water; alcohols such as ethanol, methanol and the like; and polar aprotic solvents such as acetone, dimethyl formamide, dimethyl sulfoxide and the like; and other organic solvents. Among these, it is preferable to employ a mixed solvent of water and alcohol, and more preferable to employ a mixed solvent of water and methanol.

The using amount of the solvent may be, for example, about 0.001 to 1 fold by mass with respect to the compound represented by the general formula (II), and preferably 0.01 to 0.02 fold by mass.

The reaction temperature may be set as, for example, ranging from about −20 degrees C. to the boiling point of the solvent, and may be equal to or higher than 20 degrees C., in view of the reaction kinetics. On the other hand, the reaction temperature may also be equal to or lower than 100 degrees C. in view of the stability of the reaction product. Alternatively, the reaction temperature may be equal to or lower than 0 degrees C. in view of the stability of the reaction product.

Also, the reaction time can be determined according to the reaction temperature, a stirring efficiency and the like, and may be, for example, determined as ranging from 12 to 24 hours.

In the meantime, in the process step 11, the structure of the compound represented by the general formula (V) as the product can be controlled by controlling the type of the solvent or pH of the solvent and the loading ratio of the raw materials. More specifically, selective allocation of the —$CH_2CH_2CH_2CH(N(R^5)_2)COOR^6$ group between $R^7$ and $R^8$ can be suitably controlled, such that one of desmosine derivative and isodesmosine derivative can be selectively produced.

For example, when a mixed solvent of water and methanol is employed, the proportion of ethanol over water can be selected to be larger than 0 times by volume and equal to or smaller than 10 times by volume, and the compound represented by the general formula (III) is employed at an amount of equal to or larger than 1 molar equivalent and equal to or smaller than 20 molar equivalents with respect to the compound represented by the general formula (II), such that the compound, in which $R^8$ is the —$CH_2CH_2CH_2CH(N(R^5)_2)COOR^6$ group and $R^7$ is hydrogen atom, or namely isodesmosine derivative, can be synthesized preferentially over desmosine derivative.

On the other hand, both desmosine derivative and isodesmosine derivative can be synthesized by selecting water for the solvent in the process step 11. On this occasion, for example, the compound represented by the general formula (III) is employed at equal to or larger than 1 molar equivalent and equal to or smaller than 10 mol equivalent with respect to the compound represented by the general formula (II), such that both desmosine derivative and isodesmosine derivative can be synthesized.

In the next, the process step 12 will be described.

In the process step 12, the compound represented by the general formula (I) is obtained by deprotecting carboxyl group and amino group in the compound of the general formula (V) obtained in the process step 11.

Known methods may be employed for the deprotection depending upon the types of the protective groups of $R^3$ to $R^6$.

For example, when both $R^3$ in the general formula (II) and $R^5$ in the general formula (III) are Boc group, $R^4$ in the general formula (II) is $^tBu$ group, and $R^6$ in the general formula (III) is Bn group, a catalytic reduction, for example, using hydrogen and palladium carbon (Pd/C), is carried out to remove Bn group. The conditions of the catalytic reduction is set as, for example, Pd/C 500 mol/%, at room temperature (namely 25 degrees C., and hereinafter using this temperature), for 24 hours.

Then, an acid treatment with, for example, an aqueous solution of trifluoroacetic acid (TFA) or the like, may be employed to remove $^tBu$ group and Boc group. The conditions of the acid treatment is set as, for example, TFA/water=95/5, at room temperature, for 2 hours.

On the other hand, when $R^3$ in the general formula (II) and $R^5$ in the general formula (III) are all Boc group, and $R^4$ in the general formula (II) and $R^6$ in the general formula (III) are all $^tBu$ group, then, for example, an acid treatment with an aqueous solution of trifluoroacetic acid (TFA) may be conducted to remove $^tBu$ group and Boc group in the same process step. The conditions of the acid treatment is set as, for example, TFA/water=95/5, at room temperature, for 2 hours.

In the present embodiment, prior to the process step 11, the following process step 10 may be conducted.

(Process Step 10) A process step for converting a compound represented by the general formula (VI) or a salt thereof into the compound represented by the general formula (II) or a salt thereof.

[Chem. (18)]

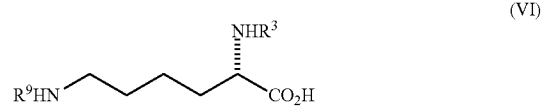

(VI)

(Wherein in the above-described general formula (VI), $R^3$ is identical to $R^3$ in the above-described general formula (II), $R^9$ is Boc group or Cbz group, and is a group that is different from $R^3$.)

The process step 10 includes, for example, the following process step.

(Process Step 10-1) A process step for converting the compound represented by the general formula (VI) into a compound represented by the following general formula (VII); and (Process Step 10-2) a process step for converting the compound represented by the general formula (VII) into the compound represented by the general formula (II) or a salt thereof.

[Chem. (19)]

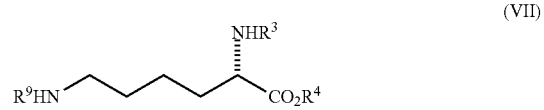

(VII)

The process step 10-1 is a process step for protecting carboxyl group in the compound represented by the formula (VI). Known methods may be employed for this process step depending upon the types of the protective group $R^4$.

Commercially available compounds may be employed for the compound represented by the formula (VI). On the other hand, when $R^4$ is, for example, $^tBu$ group, it is preferable to conduct t-butylation through a reaction with urea, like a method as discussed later in Examples.

Also, the process step 10-2 is a process step for removing the amino protective group $R^9$ from the compound represented by the formula (VII). Known methods may also be employed for this process step depending upon the types of the protective group $R^9$.

When $R^9$ is, for example, Cbz group, Cbz group may be removed through a catalytic reduction with hydrogen and palladium carbon (Pd/C). The conditions of the catalytic reduction is set as, for example, Pd/C 5 mol/%, at room temperature, for 2 hours.

On the other hand, when $R^9$ is Boc group, it is preferable to conduct a removing method with TFA.

The compound obtained in the process step 10 may be employed as a raw material in the process step 11.

The present embodiment provides the advantageous effect which is similar to that of First Embodiment.

Also, according to the present embodiment, the amino acid derivative represented by the general formula (II) and the amino acid aldehyde represented by (III) are employed as the raw materials, and Chichibabin pyridine synthesis with a lanthanoid compound serving as the catalyst is employed as the key reaction, so that desmosine, isodesmosine and derivatives thereof can be obtained with reduced number of steps and improved yield. This also allows stably creation of pyridine ring and suitable control of the location of the biding site of side-chain in pyridine ring.

Third Embodiment

In the above described embodiments, one, or two or more of hydrogen atom, one, or two or more of carbon atom, or one, or two or more of nitrogen atom in the compound represented by the general formula (I) or a salt thereof may be substituted with their isotope. For example, one, or two or more of hydrogen atom may be substituted with deuterium (D). Also, one, or two or more of carbon atom ($^{12}C$) may be substituted with $^{13}C$. Also, one, or two or more of atomic nitrogen ($^{14}N$) may be substituted with $^{15}N$. A compound that can be used as a COPD biomarker is stably obtainable by isotopic-labeling the compound represented by the general formula (I) with deuterium and the like.

Element(s) to be isotopic-labeled may be of one type, or may be of two or more types. Also, number of isotopic-labeled atoms in the compound is not particularly limited. For example, when the compound represented by the general formula (I) or a salt thereof is employed as a biomarker in the mass spectrometry measurement, the molecular weight of the isotopic-labeled compound is designed as, for example, being larger than the molecular weight of the compound without the isotopic-labeling by equal to or larger than 3, or preferably equal to or larger than 4.

Also, while the location of the isotopic-labeling site is not particularly limited, it is preferable to isotopic-label a side-chain that binds to a carbon atom constituting a pyridine ring, rather than to isotopic-label a side-chain of 1-position (N-position) of the pyridine ring, in view of easiness in the removal of side-chain. Alternatively, isotopic-substitution for nitrogen or carbon atom constituting the pyridine ring may be carried out.

For example, when one, or two or more of hydrogen atom is(are) substituted with deuterium, the position to be deuterated is not particularly limited, and it is preferable to deuterate a hydrogen atom in a side-chain binding to a pyridine ring, and it is more preferable to deuterate a hydrogen atom in a side-chain binding to a carbon atom constituting the pyridine ring, and it is furthermore preferable to deuterate a hydrogen atom binding to a carbon atom constituting a principal chain in the side-chain binding to the carbon atom constituting pyridine ring.

The isotopic-labeling method will be further specifically described below, in reference to Second Embodiment.

While the type of the method for the isotopic-labeling is not particularly limited, the following methods presented as Schemes 1 to 3, for example, will be described. In Schemes 1 to 3, a solid black dot (•) represents $^{13}C$.

Scheme 1. isodesmosine- $^{13}C_3$, $d_1$

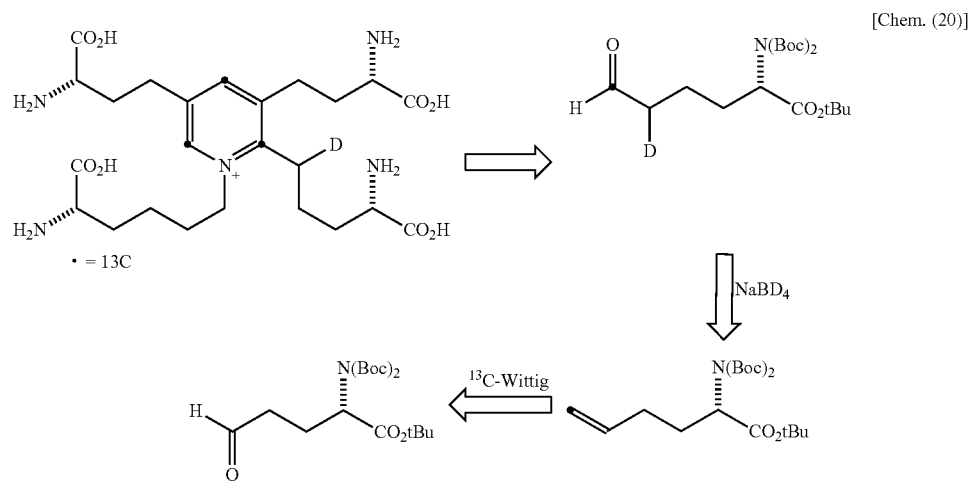

[Chem. (20)]

Scheme 1 is for describing examples, in which $^{13}C$ and D are introduced in the compound represented by the formula (I). In Scheme 1, respective one of D and $^{13}C$ are introduced in an allysine protective product, more specifically in the compound represented by the general formula (III).

While the specific example of the synthesis of the compound represented by the general formula (III) will be described in Examples, $^{13}C$ is introduced in, for example, Wittig reaction, and D is introduced in the β-position by the hydroboration oxidation, in the preparation process for the compound represented by the general formula (III).

Then, in the process step 11, the above-described isotopic-labeled compound is employed as the compound represented by the general formula (III), so that the isotopic-substitution of the carbon atom constituting of pyridine ring can be achieved and the hydrogen atom in the side-chain binding to the carbon atom constituting the pyridine ring can be deuterated.

Scheme 2. isodesmosine- $^{13}C_3$, $^{15}N_1$

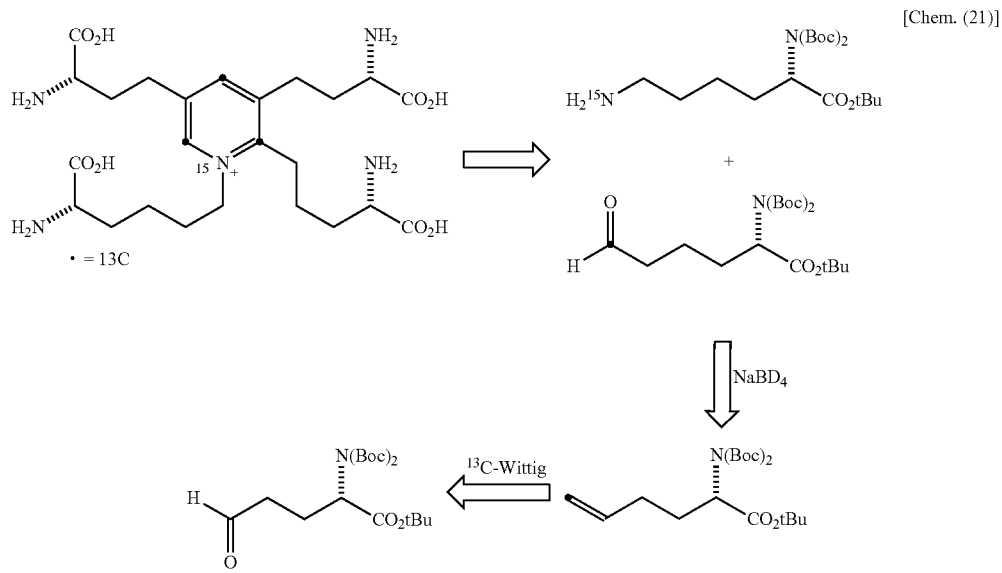

Scheme 2 is for describing examples, in which $^{13}C$ and $^{15}N$ are introduced in the compound represented by the formula (I). In Scheme 2, single $^{13}C$ is introduced in an allysine protective product, more specifically in the compound represented by the general formula (III), and $^{15}N$ is introduced in a lysine protective product, more specifically in the compound represented by the general formula (II). In this method, $^{13}C$ is introduced in the allysine protective product in Wittig reaction, and the resultant product thereof and a commercially available lysine protective product containing $^{15}N$ are employed to synthesize the compound represented by the formula (I). Since this does not employ D, this is preferable in view of inhibiting an easy reduction of the isotope rate.

Then, in the process step 11, the above-described isotopic-labeled compounds are employed as the compound represented by the general formula (II) and the general formula (III), respectively, so that the carbon atom and the nitrogen atom constituting the pyridine ring can be isotopic-substituted.

Scheme 3. isodesmosine-d$_4$

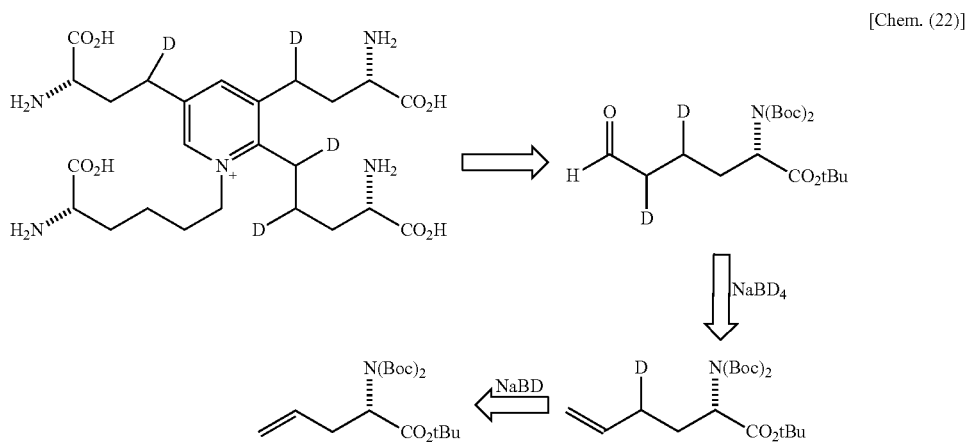

Scheme 3 is for describing examples, in which four Ds are introduced in the compound represented by the formula (I). In Scheme 3, two Ds are introduced in an allysine protective product, namely the compound represented by the general formula (III). Typical introducing method includes, for example, a method for conducting two cycles of hydroboration oxidations from asparaginic acid or glutamic acid.

Then, in the process step 11, the above-described deuterated compound can be employed as the compound represented by the general formula (III) to allow deuteration of hydrogen atom in side-chain that binds to carbon atom constituting pyridine ring.

While embodiments of the present invention have been described above, it is intended to present these embodiments for the purpose of illustrations of the present invention only, and various modifications other than that described above are also available.

The present invention includes the following embodiments.

[1] A process for preparing a compound represented by the following general formula (I) or a salt thereof:

[Chem. (23)]

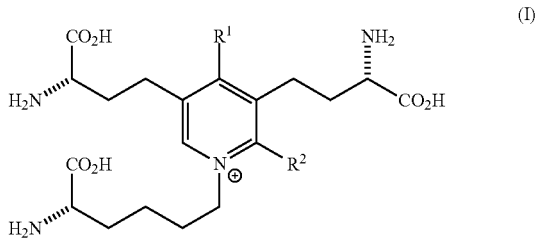
(I)

(Wherein, in the above-described general formula (I), one of $R^1$ and $R^2$ is $-CH_2CH_2CH_2CH(NH_2)COOH$ group, and the other is hydrogen atom. And wherein, in the above-described general formula (I), one, or two or more of hydrogen atom, one, or two or more of carbon atom, or one, or two or more of nitrogen atom may be substituted with their isotope.) the process comprising:

reacting a compound represented by the following general formula (II) or a salt thereof with a compound represented by the following general formula (III) in the presence of a lanthanoid compound represented by the following general formula (IV) to create a compound represented by the following general formula (V) or a salt thereof; and converting the compound represented by the general formula (V) or the salt thereof into the compound represented by the general formula (I) or a salt thereof.

[Chem. (24)]

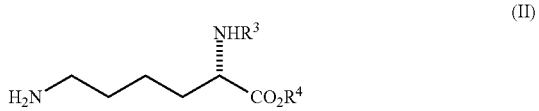
(II)

(Wherein, in the above-described general formula (II), $R^3$ is tert-butyloxycarbonyl group or benzyloxycarbonyl group, and $R^4$ is tert-butyl group, benzyl group, methyl group or ethyl group. And wherein, in the above-described general formula (II), one, or two or more of hydrogen atom, one, or two or more of carbon atom, or one, or two or more of nitrogen atom may be substituted with their isotope.)

[Chem. (25)]

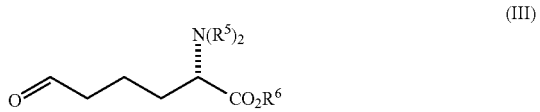
(III)

(Wherein, in the above-described general formula (III), each of $R^5$ is independently tert-butyloxycarbonyl group or benzyloxycarbonyl group, and $R^6$ is tert-butyl group, benzyl group, methyl group or ethyl group. And wherein, in the above-described general formula (III), one, or two or more of hydrogen atom, one, or two or more of carbon atom, or one, or two or more of nitrogen atom may be substituted with their isotope.)

$$Ln(OTf)_3 \quad (IV)$$

(Wherein, in the above-described general formula (IV), Ln is La, Pr, Nd, Gd, Sc, Y, Dy, Er or Yb, and Tf is trifluoromethyl sulphonyl group.)

[Chem. (26)]

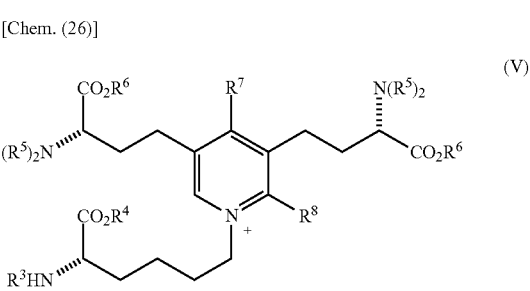
(V)

(Wherein, in the above-described general formula (V), $R^3$ and $R^4$ are identical to $R^3$ and $R^4$ in the general formula (II), respectively, and $R^5$ and $R^6$ are identical to $R^5$ and $R^6$ in the general formula (III), respectively. And wherein, one of $R^7$ and $R^8$ is a $-CH_2CH_2CH_2CH(N(R^5)_2)COOR^6$ group and the other is hydrogen atom, and, $R^5$ and $R^6$ are identical to $R^5$ and $R^6$ in the general formula (III), respectively. And wherein, in the above-described general formula (V), one, or two or more of hydrogen atom, one, or two or more of carbon atom, or one, or two or more of nitrogen atom may be substituted with their isotope.)

[2] The preparation process according to [1], further comprising converting a compound represented by the general formula (VI) or a salt thereof into the compound represented by the general formula (II) or a salt thereof.

[Chem. (27)]

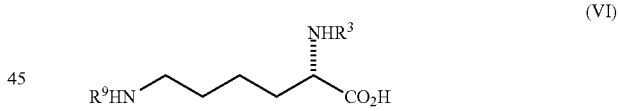
(VI)

(Wherein, in the above-described general formula (VI), $R^3$ is identical to $R^3$ in the above-described general formula (II), $R^9$ is tert-butyloxycarbonyl group or benzyloxycarbonyl group, and is a group that is different from $R^3$.)

[3] The preparation process according to [1] or [2], in which the creating the compound represented by the general formula (V) is conducted in a mixed solvent of an alcohol and water.

EXAMPLES

In the following examples, identifications of the compounds obtained in each of the process steps were carried out by NMR measurement and MS measurement.

Synthesis Example 1

In this example, a compound 6 which was a protected allysine was synthesized by a process represented by the following Scheme 4.

Scheme 4

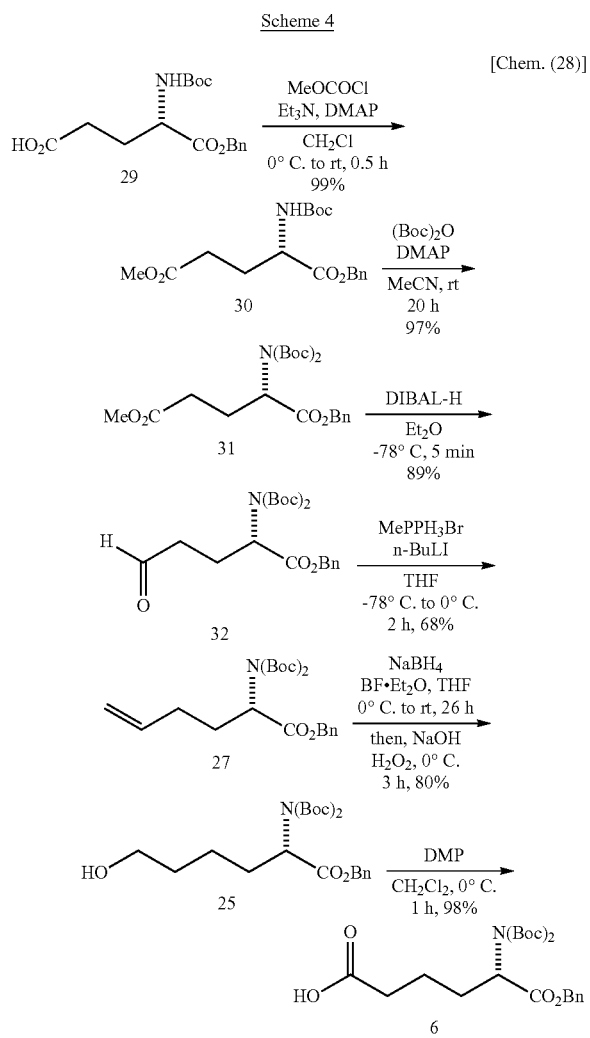

Firstly, in conformity to the method described by Yohei Koseki and other 2 authors, entitled "Efficient synthesis of benzyl 2-(S)-[(tert-butoxycarbonyl)amino]-ω-iodoalkanoates", Tetrahedron: Asymmetry, 2011, Vol. 22, pp. 580 to 586, a compound 29 was employed as a starting material to create a compound 25.

Synthesis of Compound 30

1.5 equivalent of triethylamine ($Et_3N$) was added to a $CH_2Cl_2$ (50 mL) solution of a compound 29 (5.00 g, 1.0 equivalent), which was a commercially available protected glutamic acid, and the resultant mixture was cooled to 0 degree C. Then, N,N-dimethyl-4-aminopyridine (DMAP, 0.1 equivalent) and MeOCOCl (1.2 equivalent) were sequentially added. The obtained solution was warmed to the room temperature, and was stirred for 0.5 hour. The reaction mixture was diluted in $CH_2Cl_2$, and was washed with 1M aqueous solution of $NaHCO_3$, and then was extracted for three times in $CH_2Cl_2$. The obtained organic layer was dried with $Na_2SO_4$. Purification was made through a silica gel column chromatography (hexane/EtOAc=2/1) to obtain 5.16 g of the compound 30 (99% yield) that was a colorless oily material.

Synthesis of Compound 31

DMAP (0.2 equivalent) was added to a MeCN (3.0 mL) solution of the compound 30 (0.50 g, 1.0 equivalent). A MeCN (2.0 mL) solution of $(Boc)_2O$ (4.0 equivalent) was added to the obtained mixture, and the mixture was stirred at the room temperature for 20 hours. Purification was made through the silica gel column chromatography (hexane/EtOAc=3/1) to obtain 0.62 g of the compound 31 (97% yield) that was a colorless oily material.

Synthesis of Compound 32

An $Et_2O$ (6.2 mL) solution of the compound 31 (2.00 g, 1.0 equivalent) was cooled to −78 degrees C., and hydrogenated diisobutylaluminum (DIBAL-H, 1M solution in hexane, 1.4 equivalent) was dropped thereto for 3 minutes. The reaction mixture was stirred for 5 minutes, and then water (150 μL) was added to stop the reaction, and the mixture was warmed back to the room temperature. The obtained white thick liquid was filtered with Celite (registered trademark) powder, and was washed for three times in $Et_2O$. The filtrate was concentrated, and very small amount of water remained therein was removed by an azeotropy with toluene. It was purified through the silica gel column chromatography (hexane/EtOAc=5/1) to obtain 1.66 g of the compound 32 (89% yield) that was a colorless oily material.

Synthesis of Compound 27

In this Example, a carbon atom increase of the compound 32 was achieved by the Wittig reaction to obtain the compound 27. More specifically, n-BuLi (2.64 M solution in hexane, 1.1 equivalent) was dropped to a THF (20 mL) suspension of methyl triphenylphosphine bromide ($MePPh_3Br$, 807 mg, 1.2 equivalent), at −78 degrees C. It was warmed up to 0 degree C., and the obtained mixture was stirred for 1.5 hours, and then a THF (10 mL) solution of the compound 32 (0.793 g, 1.0 equivalent) was added to the obtained ylide solution. It was stirred at 0 degree C. for 0.5 hours, and then the reaction was stopped with the saturated $NH_4Cl$ aqueous solution. The extractions were made for three times in EtOAc. The organic layers were gathered and dried with $Na_2SO_4$. It was purified through the silica gel column chromatography (hexane/EtOAc=19/1) to obtain 0.54 g of the compound 27 (68% yield) that was a colorless oily material.

Synthesis of Compound 25

A THF (3.0 mL) solution of the compound 27 (0.455 g, 1.0 equivalent) was cooled to 0 degree C., and $NaBH_4$ (1.3 equivalent) was added thereto. After being stirred for 10 minutes, $BF_3.Et_2O$ (1.3 equivalent) was added to this solution. The mixture was warmed to the room temperature, and was stirred for 26 hours. Then, the solution was cooled to 0 degree C., and 1M NaOH (1.5 equivalent) was added, and then 30% $H_2O_2$ (1.33 mL) was added and stirred for 3 hours. The mixture was diluted with water, and the extractions were made for three times in EtOAc. The organic layers were gathered and dried with $Na_2SO_4$. It was purified through the silica gel column chromatography (hexane/EtOAc=1/1) to obtain 0.377 g of the compound 25 (80% yield) that was a colorless oily material.

Synthesis of Compound 6 (2-(S)-Bis-tert-butoxycarbonylamino-6-oxo-hexanoic acid benzyl ester)

In this example, the compound 6 was obtained via Dess-Martin oxidation of the compound 25.

More specifically, the compound 25 (100 mg, 0.229 mmol) was dissolved in dichloromethane (2.86 mL), and after being cooled to 0 degree C., DMP (Dess-Martin periodinane, 145.4 mg, 0.343 mmol) was added and was stirred for 1 hour. A solution of sodium bicarbonate/sodium thiosulfate=1/1 was added to stop the reaction, and the extraction was made with ethyl acetate. The extracted organic layer was dried with sodium sulfate, and was concentrated under a reduced pressure, and the residue was isolated and purified through the silica gel column chromatography (hexane/ethyl acetate=4/1) to obtain the compound 6 at 98% (97.6 mg).

Synthesis Example 2

In this example, the compound 54 (2-(S)-Bis-tert-butoxy-carbonylamino-6-oxo-hexanoic acid tert-butyl ester), which is a protected allysine, was synthesized.

Synthesis Example 2-1

The compound 54 was obtained by the following reaction formula.

[Chem. (29)]

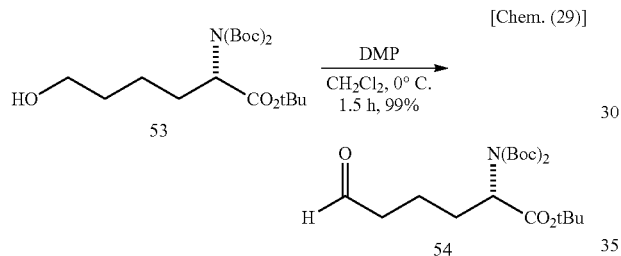

A compound 53 was obtained in conformity to the Synthesis Example 1, Then, the obtained compound 53 (104 mg, 0.258 mmol) was dissolved in dichloromethane (3.1 mL), and after being cooled to 0 degree C., DMP (Dess-Martin periodinane, 157.7 mg, 0.378 mmol) was added and was stirred for 1.5 hour. A solution of sodium bicarbonate/sodium thiosulfate=1/1 was added to stop the reaction, and the extraction was made with ethyl acetate. The extracted organic layer was dried with sodium sulfate, and was concentrated under a reduced pressure, and the residue was isolated and purified through the silica gel column chromatography (hexane/ethyl acetate=4/1) to obtain the compound 54 at 99% (103 mg).

Synthesis Example 2-2

The compound 53 was synthesized by the procedure shown in the following Scheme 5, and the compound 54 was obtained from the obtained compound 53.

Scheme 5

[Chem. (30)]

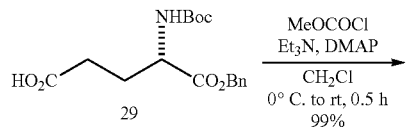

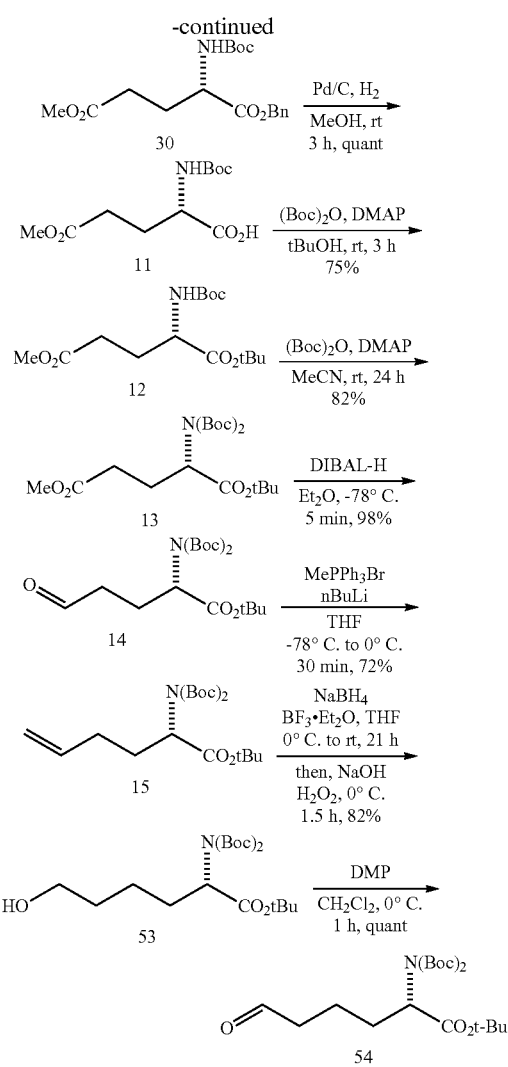

Synthesis of N-[(1,1-Dimethylethoxy)carbonyl]-5-methyl-1-(phenylmethyl) ester (Compound 30)

The compound 30 was synthesized as shown in the following formula.

[Chem. (31)]

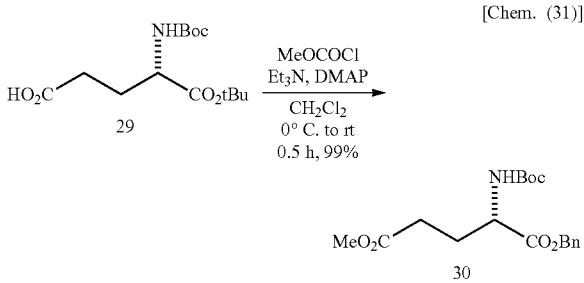

The compound 29 (5.1 g) was dissolved in CH$_2$Cl$_2$ (40 mL), and Et$_3$N (1.5 equivalent) was added thereto, and the mixture was cooled to 0 degree C. Next, DMAP (0.1 equivalent) and MeOCOCl (1.2 equivalent) were added, and then, was warm up to the room temperature, and was stirred for 0.5 hour. The reaction solution was diluted with $CH_2Cl_2$, and was washed with 1M $NaHCO_3$ solution, and then the extraction was made with $CH_2Cl_2$. Then, the obtained organic layer was dried with $Na_2SO_4$, and then was purified through the silica gel chromatography (hexane/EtOAc=2/1) to obtain 5.26 g of the compound 30 (99% yield) that was a colorless oily material.

Synthesis of
N-[(1,1-Dimethylethoxy)carbonyl]-5-methyl ester (compound 11)

The compound 11 was synthesized as shown in the following formula.

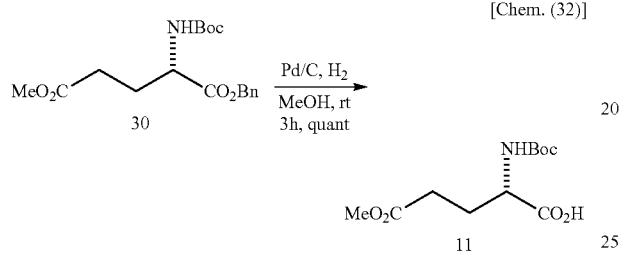

[Chem. (32)]

The compound 30 (487 mg) was dissolved in MeOH (2.9 mL), and then 10% by weight of Pd/C (1.0% by mol) was added. It was stirred in the hydrogen atmosphere at the room temperature for 3 hours. A solid material in the reaction solution was removed by a Celite filtration, and the concentration under the reduced pressure was carried out to obtain 362 mg of the compound 11 (100% yield).

Synthesis of N-[(1,1-Dimethylethoxy)carbonyl]-1-(1,1-dimethylethyl)-5-methyl ester (Compound 12)

The compound 12 was synthesized as shown in the following formula.

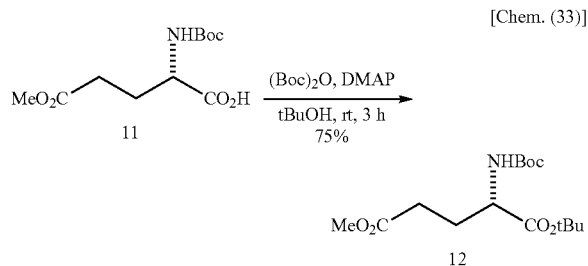

[Chem. (33)]

A tBuOH (17.9 mL) solution of $(Boc)_2O$ (1.2 equivalent), and DMAP (0.1 equivalent) were added sequentially to a tBuOH (35.8 mL) solution of the compound 11 (7.01 g). After stirring for 3 hours at the room temperature, the purification was made through the silica gel chromatography (hexane/EtOAc=8/1) to obtain 6.37 g of the compound 12 (75% yield) that was a colorless oily material.

Synthesis of N,N-Bis[(1,1-dimethylethoxy)carbonyl]-1-(1,1-dimethylethyl)-5-methyl ester (Compound 13)

The compound 13 was synthesized as shown in the following formula.

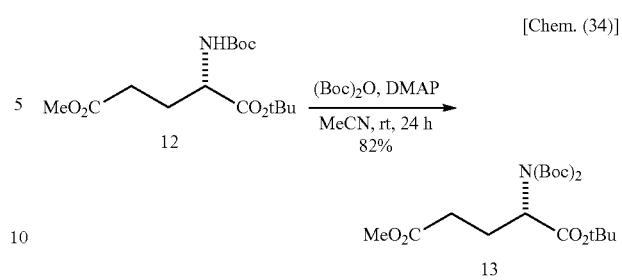

[Chem. (34)]

The compound 12 (2.27 g) was dissolved in MeCN (20 mL), and then DMAP (0.2 equivalent) was added thereto, and further, MeCN (8 mL) solution of $(Boc)_2O$ (4.0 equivalent) was added. After stirring for 24 hours at the room temperature, the purification was made through the silica gel chromatography (hexane/EtOAc=8/1) to obtain 2.31 g of the compound 13 (82% yield) as a colorless oily material.

Synthesis of N,N-Bis[(1,1-dimethylethoxy)carbonyl]-5-oxo-1,1-dimethylethyl ester (Compound 14)

The compound 14 was synthesized as shown in the following formula.

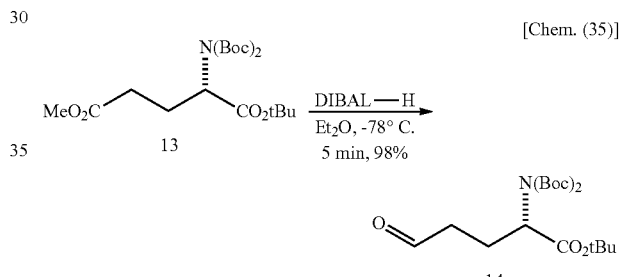

[Chem. (35)]

The compound 13 (184 mg) was dissolved in $Et_2O$ (4.5 mL), and then was cooled to −78 degrees C. Then, DIBAL-H (1.4 equivalent) was slowly added and was stirred for 5 minutes. Afterwards, water (150 µL) was added to stop the reaction. The obtained reaction solution was purified by the Celite filtration. Further purification was made through the silica gel chromatography (hexane/EtOAc=4/1) to obtain 152 mg of the compound 14 (98% yield) as a colorless oily material.

Synthesis of N,N-[Bis[(1,1-dimethylethoxy)carbonyl]amino]-1,1-dimethylethyl ester (Compound 15)

The compound 15 was synthesized as shown in the following formula.

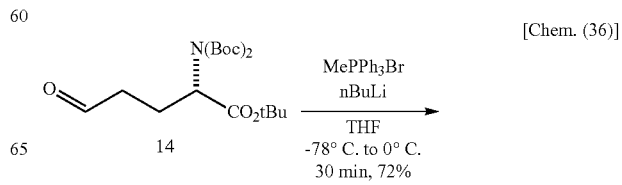

[Chem. (36)]

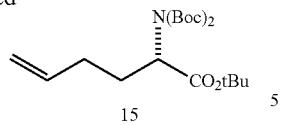

15 n-BuLi (1.1 equivalent) was added to a THF (16 mL) solution of MePPh$_3$Br (1.2 equivalent) at −78 degrees C. Afterwards, it was stirred at 0 degree C. for 1.5 hour. It was cooled again to −78 degrees C., and then THF (8.2 mL) of the compound 14 (650 mg) was added to the reaction solution. It was warmed to 0 degree C., and was stirred for 0.5 hour. Then, after the reaction was stopped with the saturated NH$_4$Cl aqueous solution, the extractions were made for three times in EtOAc. The organic layer was dried with Na$_2$SO$_4$, and then was purified through the silica gel chromatography (hexane/EtOAc=20/1) to obtain 476 mg of the compound 15 (72% yield) that was a colorless oily material.

Synthesis of tert-Butyl-2-(S)-[bis-(tert-butoxycarbonyl)-amino]-6-hydroxyhexanoate (Compound 53)

The compound 53 was synthesized as shown in the following formula.

[Chem. (37)]

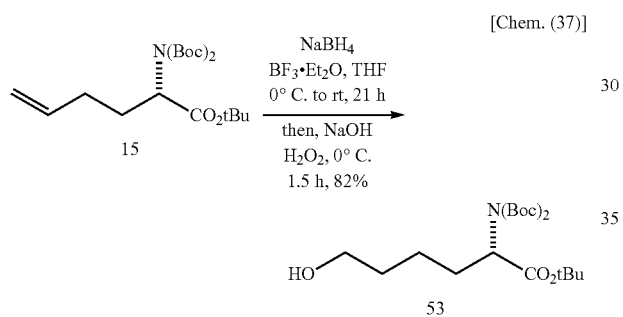

A THF (5.38 mL) solution of the compound 15 (437 mg) was cooled to 0 degree C., and then NaBH$_4$ (1.3 equivalent) was added. After stirring for 10 minutes, BF$_3$.Et$_2$O (1.3 equivalent) was further added, and was stirred at the room temperature for 21 hours. Then, it was cooled to 0 degree C. again, and after that, 1M NaOH (1.5 equivalent) and 30% H$_2$O$_2$ (1.41 mL) were sequentially added. After the mixture was diluted with water, the extractions were made for three times in EtOAc. After being dried with Na$_2$SO$_4$, purification was made through the silica gel chromatography (hexane/EtOAc=2/1) to obtain 376 mg of the compound 53 (82% yield) that was a white crystal.

Synthesis of N,N-Bis[(1,1-dimethylethoxy)carbonyl]-6-oxo-1,1-dimethylethyl ester (Compound 54)

The compound 54 was synthesized as shown in the following formula.

[Chem. (38)]

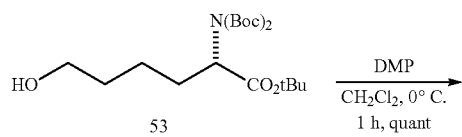

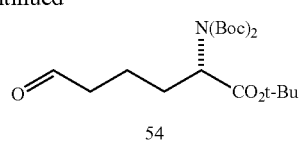

54

The compound 53 (81.5 mg) was dissolved in CH$_2$Cl$_2$ (2.5 mL), and then DMP (1.5 equivalent) was added while being cooled to 0 degree C. Then, after being stirred for 1 hour, a solution of NaHCO$_3$/Na$_2$S$_2$O$_3$=1:1 was added to stop the reaction. Next, extractions were made for three times with EtOAc, and then it was dried with Na$_2$SO$_4$. Then, purification was made through the silica gel chromatography (hexane/EtOAc=4/1) to obtain 89.1 mg of the compound 54 (100% yield) that was a white crystal.

The process of the present example allows obtaining the compound of the formula 54 without employing urea-related compounds.

Example 1

In the present Example, total synthesis of isodesmosine was carried out by employing the compound 6 obtained in the Synthesis Example 1.

Synthesis of Compound 4 (6-Benzyloxycarbonylamino-2-(S)-tert-butoxycarbonylamino-hexanoic acid tert-butyl ester)

[Chem. (39)]

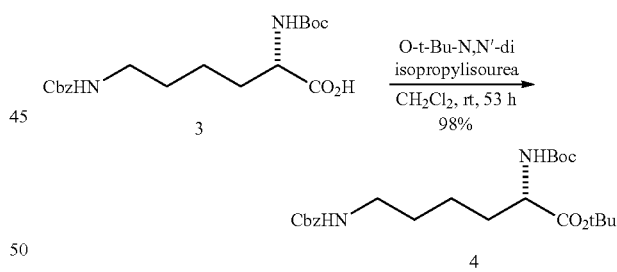

A commercially available compound 3 (1.00 g, 2.62 mmol) was dissolved in dichloromethane (5.00 mL), and after being cooled to 0 degree C., O-tBu-N, N'-diisopropyl isourea (1.57 g, 1.77 mL, 7.88 mmol) was added thereto. The mixture was warmed back to the room temperature and was stirred for 27 hours, and then, O-tBu-N, N'-diisopropyl isourea (1.57 g, 1.77 mL, 7.88 mmol) was added again, and was stirred for 26 hours. The reaction solution was concentrated under the reduced pressure and the solvent was distilled away, and then a solid material was removed through a short column. The residue was isolated and purified through the silica gel column chromatography (hexane:ethyl acetate=2:3) to obtain the compound 4 at 98% (1.1278 g).

Synthesis of Compound 5 (6-Amino-2-(S)-tert-butoxycarbonylamino-hexanoic acid tert-butyl ester)

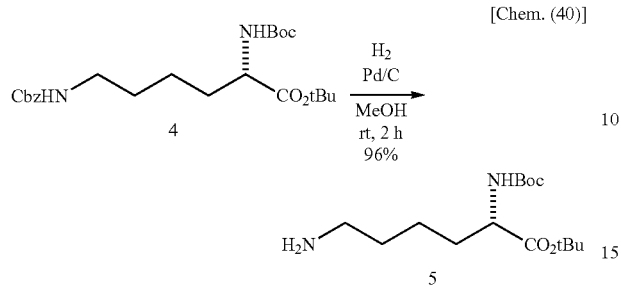

[Chem. (40)]

The compound 4 (98.8 mg, 0.226 mmol) and 10% Pd/C (12.1 mg, 11.4 μmol) were dissolved in methanol (1 mL), and was stirred in the hydrogen atmosphere for 2 hours at the room temperature. A solid material of the reaction solution was removed by the Celite filtration, and the concentration under the reduced pressure was carried out to obtain the compound 5 at 96% yield (66.1 mg). The resultant product was not further purified, and thus was employed for the next reaction.

Synthesis of Compound 28 (2-(4-(S)-Benzyloxycarbonyl-4-bis-tert-butoxycarbonylamino-butyl)-3,5-bis-(3-(S)-benzyloxycarbonyl-3-tert-butoxycarbonylamino-propyl)-1-(5-(S)-tert-butoxycarbonyl-5-tert-butoxycarbonylamino-pentyl)-pyridinium)

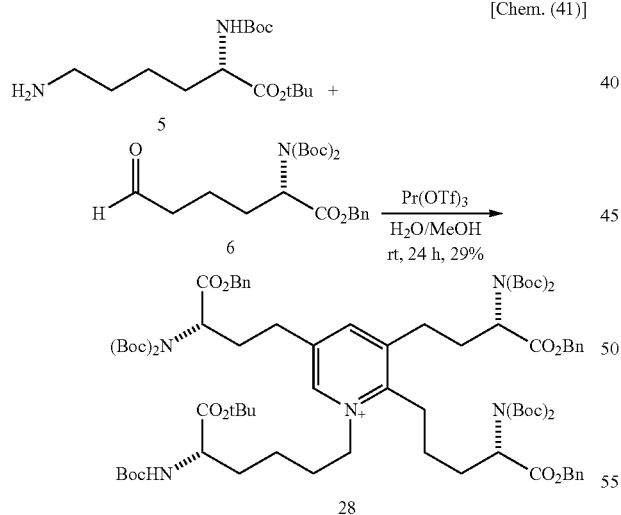

[Chem. (41)]

The compound 5 (7.2 mg, 23.8 μmol) and Pr(OTf)$_3$ (7.0 mg, 11.9 μmol) were dissolved in water (1.59 mL) and methanol (0.19 mL), and the compound 6 (40.9 mg, 93.9 μmol) that had been dissolved in methanol (0.60 mL) was added thereto. That is, in this example, a blending composition ratio between the compound 6 and the compound 5 was defined as 4/1 in a molar ratio, and water/methanol was defined as 2/1 for the reaction solvent. After being stirred for 24 hours, the extraction was made with ethyl acetate. The extracted organic layer was dried with sodium sulfate, and was concentrated under the reduced pressure, and the residue was isolated and purified with a neutral silica gel column chromatography (with 100 mL of hexane/ethyl acetate=1/1 and 50 mL of 0/1, and, 100 mL of ethyl acetate/methanol=10/1) to obtain the compound 28 at 29% (10.9 mg).

Synthesis of Compound 39 (2-(4-(5)-Bis-tert-butoxycarbonylamino-4-carboxy-butyl)-3,5-bis-(3-(S)-bis-tert-butoxycarbonylamino-3-carboxy-propyl)-1-(5-(S)-tert-butoxycarbonyl-5-tert-butoxycarbonylamino-pentyl)-pyridinium)

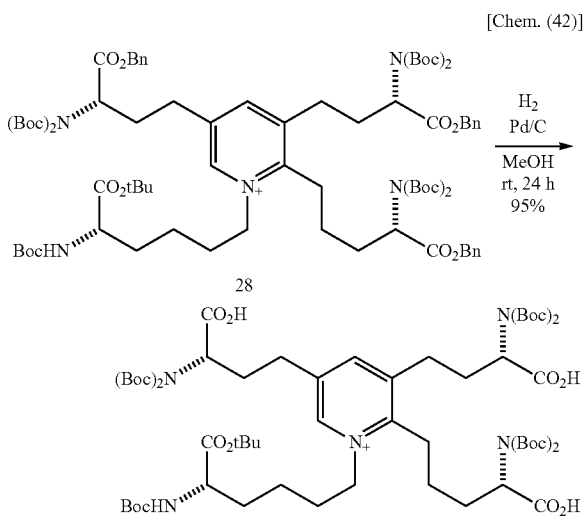

[Chem. (42)]

The compound 28 (18.7 mg, 11.0 μmol) and 10% Pd/C (64.0 mg, 60.2 μmol) were dissolved in methanol (0.3 mL), and was stirred in the hydrogen atmosphere for 24 hours. The reaction solution was filtered with a Celite and a neutral silica, and was concentrated under the reduced pressure to obtain the compound 39 at 95% (14.9 mg). The resultant product was not further purified, and thus was employed for the next reaction.

Synthesis of Compound 2 ((+)-Isodesmosine)

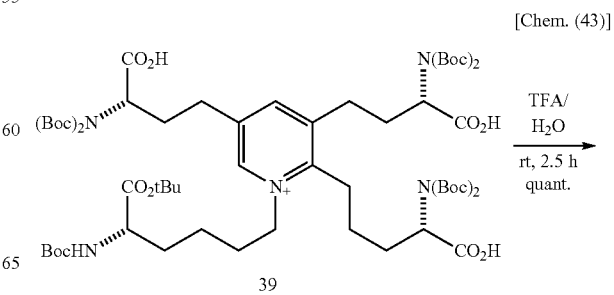

[Chem. (43)]

-continued

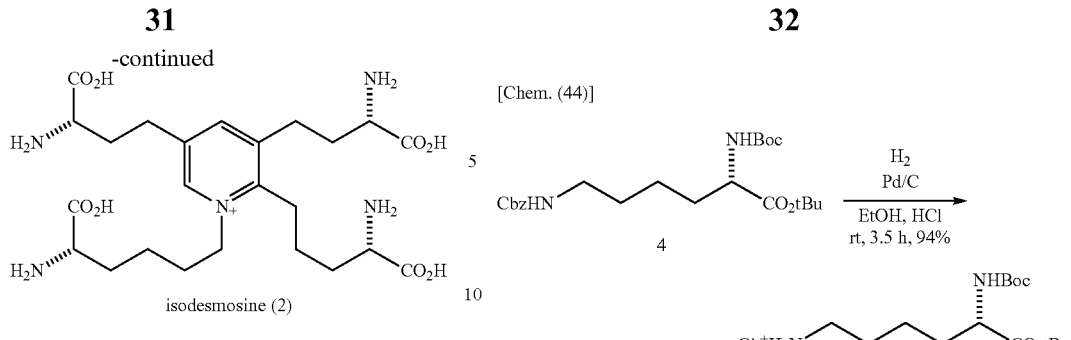

isodesmosine (2)

A mixture of TFA (trifluoroacetic acid) and distilled water (2.4 mL, TFA/water=95/5) were added to the compound 39 (14.9 mg, 10.4 μmol), and was stirred for 2.5 hours. The reaction solution was concentrated under the reduced pressure, and was isolated and purified through a reversed-phase silica gel chromatography (distilled water, containing 0.1% TFA) to obtain the compound 2 in quant. (quantitative yield, 8.1 mg).

Rf 0.28 [MeOH (0.1% TFA)/H$_2$O (0.1% TFA)=1:9]; [α]$_D^{20}$+10.6 (c 0.50, H$_2$O), $^1$H NMR (500 MHz, D$_2$O) δ 8.60 (1H, s, H6), 8.29 (1H, s, H4), 4.58 (2H, m, H7), 4.11 (1H, t, J=6.1 Hz, H20), 4.05, 4.04 (1H, t, J=6.1 Hz, H16/24), 4.01 (1H, t, J=6.1 Hz, H11), 3.12-3.18 (2H, m, H13), 3.04-3.12 (1H, m, H18), 2.97-3.04 (1H, m, H22), 2.87-2.97 (2H, m, H18/22), 2.21-2.36 (4H, m, H19/H23), 2.09-2.21 (2H, m, H15), 1.91-2.07 (4H, m, H8/H10), 1.71-1.91 (2H, m, H14), 1.48-1.68 (2H, m, H9); $^{13}$C NMR (125 MHz, D$_2$O) δ 173.1, 172.9, 172.7, 172.6 (C12/17/21/25), 154.3 (C2), 146.8 (C4), 144.0 (C6), 141.1 (C3), 139.3 (C5), 58.6 (C7), 53.6, 53.3, 53.0 (C11/16/20/24), 30.9 (C19/23), 30.3 (C15), 30.0 (C10), 29.1 (C8), 28.6 (C13), 27.9 (C18), 27.8 (C22), 24.4 (C14), 22.0 (C9); ESI-HRMS [M]+ calcd for C$_{24}$H$_{40}$N$_5$O$_8$ [M]+ 526.2877. found 526.2877.

Example 2

The solvent composition employed in Example 1 for obtaining the compound 28 from the compound 5 and the compound 6 was changed, and the synthesis reaction was conducted in conformity to Example 1.

More specifically, in relation to the reaction solvent, in place of adopting water/methanol as 2/1 in Example 1, this Example employed water/methanol as 3/1, and the other conditions were in conformity to Example 1 to synthesize the compound 28.

This also resulted in obtaining the compound 28 at 24% of yields in the present Example.

Synthesis Example 3

In this example, a compound 5' (5-(S)-tert-Butoxycarbonyl-5-tert-butoxycarbonylamino-pentyl-ammonium chloride) which was a hydrochloride salt of the compound 5 was obtained.

Synthesis Example 3-1

In the present example, the compound 4 was employed as a raw material to obtain hydrochloride salt of the compound 5: the compound 5'(5-(S)-tert-Butoxycarbonyl-5-tert-butoxycarbonylamino-pentyl-ammonium chloride).

[Chem. (44)]

The compound 4 (40.0 mg, 0.916 mmol) and 10% Pd/C (4.88 mg, 4.58 μmol) were dissolved in ethanol (0.36 mL), and 1M hydrochloric acid (0.1 mL) was added thereto, and was stirred in the hydrogen atmosphere at the room temperature for 3.5 hours. A solid material of the reaction solution was removed by the Celite filtration, and the concentration under the reduced pressure was carried out to obtain the compound 5' at 94% yield (29.2 mg). The resultant product was not further purified, and thus was employed for the next reaction.

Synthesis Example 3-2

In this example, compounds 12 and 18 were synthesized by the procedure shown in the following Scheme 6 in conformity to the method described in Synthesis Example 2-2 to further obtain the compound of formula 5'.

[Chem. (45)]

Scheme 6

Synthesis of N-[(1,1-dimethylethoxy)carbonyl]-5-hydroxy-1,1-dimethylethyl ester (Compound 18)

The compound 18 was synthesized as shown in the following formula.

[Chem. (46)]

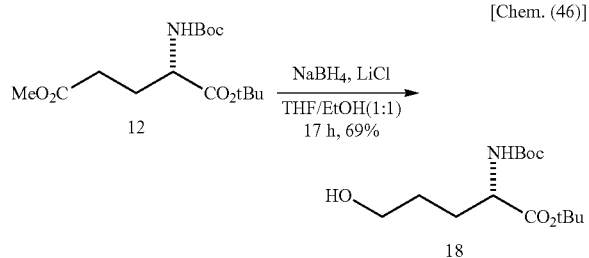

NaBH$_4$ (4.0 equivalent) was added to THF/EtOH (1:1) (10 mL) solution of LiCl (4.0 equivalent), and was stirred for 10 minutes. After being cooled to −5 degrees C., the THF (15 mL) solution of the compound 12 (475.5 mg) was slowly added. Afterwards, it was warmed to the room temperature, and was stirred for 17 hours. Water was added to stop the reaction, and then, extractions were conducted with EtOAc for three times, and the extract was dried with Na$_2$SO$_4$. Purification was made through the silica gel chromatography (hexane/EtOAc=2/1) to obtain 299.2 mg of the compound 18 (69% yield) that was a white crystal.

Synthesis of 5-bromo-N-[(1,1-dimethylethoxy)carbonyl]-1,1-dimethylethyl ester (Compound 16)

The compound 16 was synthesized as shown in the following formula.

[Chem. (47)]

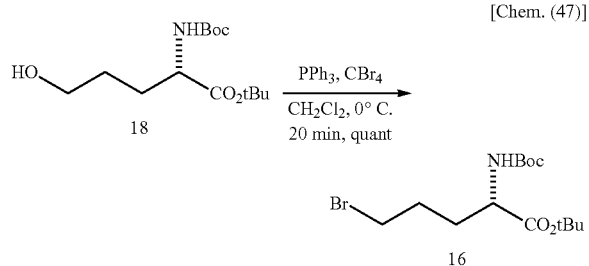

A CH$_2$Cl$_2$ (7.3 mL) solution of the compound 18 (210.2 mg) was cooled to 0 degree C., and then, CBr$_4$ (1.5 equivalent) and PPh$_3$ (2.0 equivalents) were sequentially added thereto, and the mixture was stirred for 20 minutes. The reaction was stopped with hexane/EtOAc=2:1, and purification was made through the silica gel chromatography (hexane/EtOAc=2/1) to obtain 254.6 mg of the compound 16 (100% yield) as a colorless oily material.

Synthesis of 5-cyano-2-[[(1,1-dimethylethoxy)carbonyl]amino]-1,1-dimethylethyl ester (Compound 17)

The compound 17 was synthesized as shown in the following formula.

[Chem. (48)]

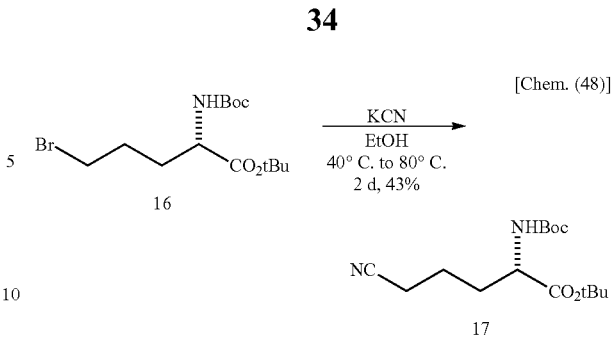

EtOH/H$_2$O (9:1) (2.49 mL) solution of KCN (1.4 equivalent) was added to EtOH (8.0 mL) solution of the compound 16 (131.2 mg), and the temperature was gradually elevated from 40 degrees C. to 80 degrees C., and the mixture was stirred for two days. Afterwards, a solid material was removed by a filtration, and then extractions were made twice with CH$_2$Cl$_2$, and it was dried with Na$_2$SO$_4$. Purification was made through the silica gel chromatography (hexane/EtOAc=10/1) to obtain 47.4 mg of the compound 17 (43% yield) as a colorless oily material.

Synthesis of 5-(S)-(tert-Butoxycarbonyl)-5-[(tert-butoxycarbonyl)-amino]-pentyl-amine hydrochloride (Compound 5')

The compound 5' was synthesized as shown in the following formula.

[Chem. (49)]

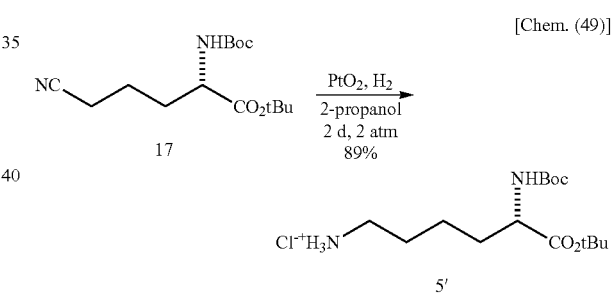

1M HCl (175 μL) and PtO$_2$ (0.1 equivalent) were sequentially added to 2-propanol (3.97 mL) solution of the compound 17 (47.4 mg), and it was stirred in the hydrogen atmosphere at 2 atom for two days. Celite filtration of the reaction solution was conducted to remove a solid material, and then concentration under the reduced pressure was carried out to obtain 48.1 mg of the compound 5' (89% yield) as a yellow oily material.

The method of the present example allowed obtaining the compound of the formula 5' without employing urea-related compounds. Total yield in the case of obtaining the compound of formula 5' from the compound of formula 12 was 26%.

Example 3

The present Example relates to the Chichibabin pyridine synthesis that allows synthesizing desmosine, isodesmosine at once.

More specifically, in the present Example, the compound 54 obtained in Synthesis Example 2 and the compound 5' obtained in Synthesis Example 3 were employed to carry out total synthesis of desmosine and isodesmosine.

Synthesis of Compound 55: (2-(4-(S)-tert-butoxy-carbonyl-4-bis-tert-butoxycarbonylamino-butyl)-3,5-bis-(3-(S)-tert-butoxycarbonyl-3-tert-butoxycarbonylamino-propyl)-1-(5-(S)-tert-butoxycarbonyl-5-tert-butoxycarbonylamino-pentyl)-pyridinium) and Compound 56: (3,5-Bis-(3-(S)-tert-butoxycarbonyl-3-tert-butoxycarbonylamino-propyl)-4-(4-(S)-tert-butoxycarbonyl-4-tert-butoxycarbonylamino-butyl)-1-(5-(S)-tert-butoxycarbonyl-5-tert-butoxycarbonylamino-pentyl)-pyridinium)

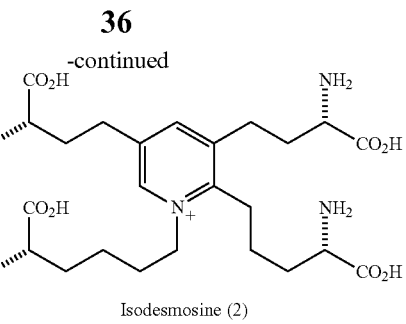

Isodesmosine (2)

A mixture of TFA (trifluoroacetic acid) and distilled water (0.78 mL, TFA/water=95/5) were added to the compound 55 (5.1 mg, 3.19 μmol), and was stirred for 2 hours. The reaction solution was concentrated under the reduced pres-

[Chem. (50)]

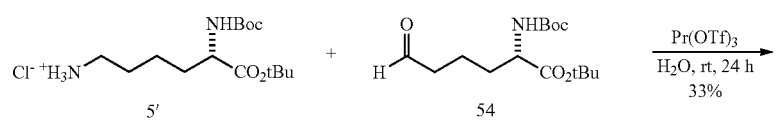

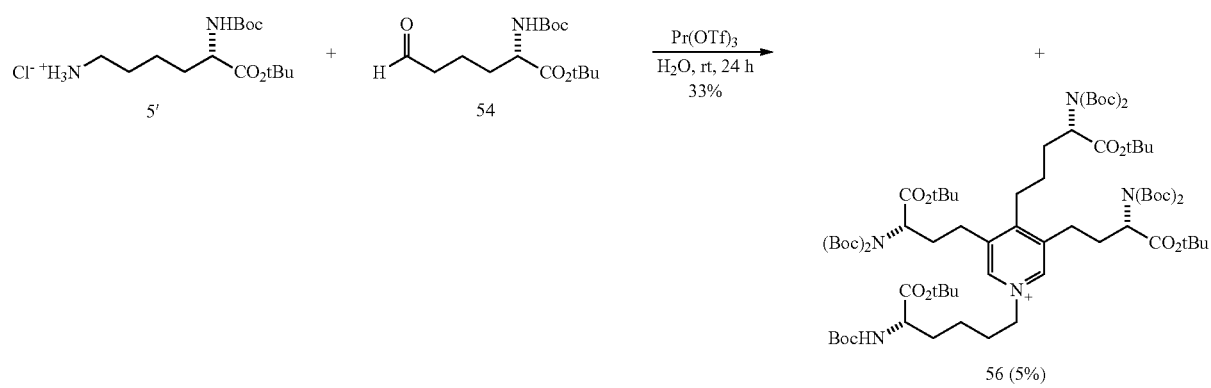

The compound 5' (7.5 mg, 22.1 μmol) and the compound 54 (38.1 mg, 94.4 μmol) were dissolved in water (1.48 mL), and Pr(OTf)$_3$ (6.5 mg, 11.1 μmol) was added thereto. After being stirred for 24 hours, an extraction was made with ethyl acetate. The extracted organic layer was dried with sodium sulfate, and was concentrated under the reduced pressure, and the residue was isolated and purified with a neutral silica gel column chromatography (with 100 mL of hexane/ethyl acetate=1/1 and 100 mL of 0/1, and 100 mL of ethyl acetate/methanol=10/1) to obtain the compound 55 at 28% (9.8 mg) and the compound 56 at 5% (1.9 mg).

Synthesis of Compound 2 (Isodesmosine)

[Chem. (51)]

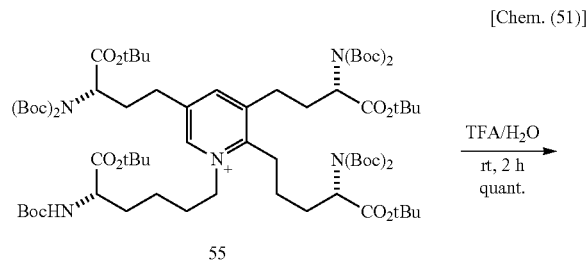

sure, and was isolated and purified through the reversed-phase silica gel chromatography (distilled water, containing 0.1% TFA) to obtain the compound 2 in quant. (2.2 mg). It was also confirmed in the present Example that the obtained compound was compound 2 from the MS spectrum and the NMR spectrum.

Synthesis of Compound 1 (Desmosine)

[Chem. (52)]

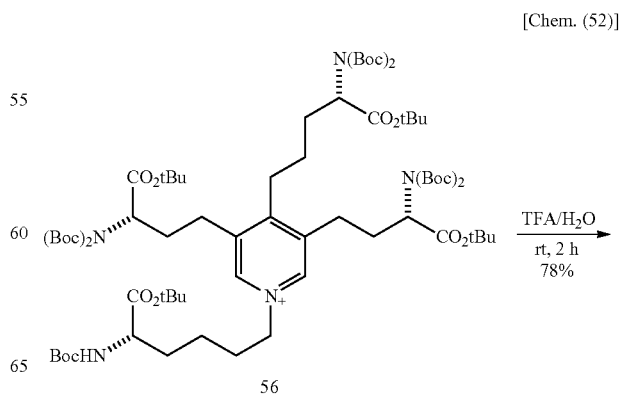

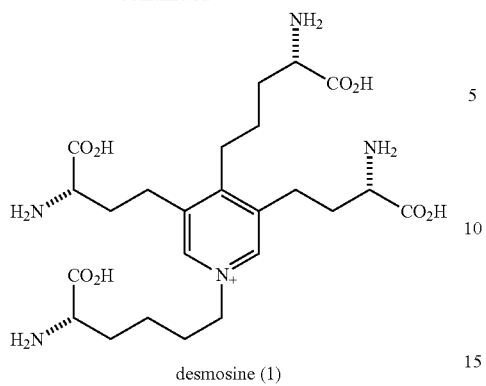

desmosine (1)

A mixture of TFA (trifluoroacetic acid) and distilled water (0.69 mL, TFA/water=95/5) were added to the compound 56 (4.5 mg, 3.1 μmol), and was stirred for 2 hours. The reaction solution was concentrated under the reduced pressure, and was isolated and purified through the reversed-phase silica gel chromatography (distilled water, containing 0.1% TFA) to obtain the compound 1 at 78% (1.4 mg).

Rf 0.22 [MeOH (0.1% TFA)/H$_2$O (0.1% TFA)=1:9], $[\alpha]^{20}_D$ +9.8 (c 0.10, H$_2$O), $^1$H NMR (D$_2$O, 500 MHz) δ 8.53 (2H, s, H2/6), 4.50 (2H, t, J=7.2 Hz, H7), 3.87-3.84 (1H, m, H20), 3.79-3.78 (1H, m, H16), 3.76-3.72, (1H, m, H11), 3.05-2.99 (2H, m, H13), 2.94-2.86 (4H, m, H18/18'), 2.18-2.13 (4H, m, H19/19'), 2.07-2.00 (4H, m, H8/15), 1.90-1.88 (2H, m, H10), 1.67-1.33 (4H, m, H9/14); $^{13}$C NMR (125 MHz, D$_2$O) δ 175.1, 174.6 (C12/17/21), 159.2 (C4), 142.3 (C2/6), 140.8 (C3/5), 63.8 (C7), 55.0, 54.9, 54.8 (011/16/20/20'), 31.7, 31.1 (C8/10/15/19/19'), 30.6 (C8), 28.9 (C13), 25.3 (C9/14); ESI-HRMS (m/z) calcd for C$_{24}$H$_{40}$N$_5$O$_8$ [M]$^+$ 526.2877. found 526.2877.

Further, loading amount of the compound 56 was determined as 6.3 mg (4.24 μmol), and deprotection reaction and purification were conducted in conformity to the above-described method and procedure. As a result, as shown in the following formula, 2.8 mg of the compound 1, namely desmosine, was obtained (yield quant.).

[Chem. (53)]

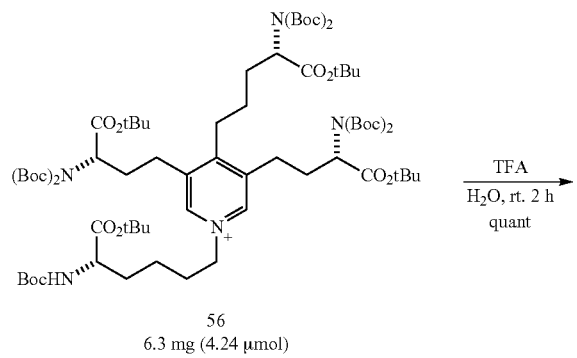

56
6.3 mg (4.24 μmol)

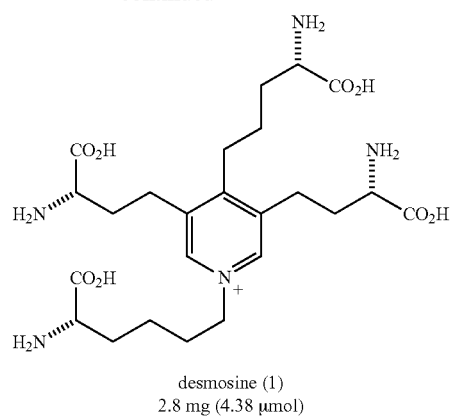

desmosine (1)
2.8 mg (4.38 μmol)

Example 4

The loading composition ratio between the compound 5' and the compound 54 in Example 3 for obtaining the compounds 55 and 56 from the compound 5' and the compound 54 was changed, and the other conditions were in conformity to Example 3 to carry out the synthesis reaction.

Also, the compound 5 used in Example 1 was also employed in place of the compound 5' and the loading composition ratio of the compound 5 and the compound 54 was changed, and the other conditions were in conformity to Example 1 to carry out the synthesis reaction.

The results are shown in Table 1. According to Table 1, it was found that the yield of the synthetic intermediate of desmosine or the synthetic intermediate of isodesmosine can be suitably controlled by controlling the loading ratio of the raw materials and the composition ratio of the solvent.

TABLE 1

| entry | ratio (54/5) | ratio (54/5') | H$_2$O/MeOH | yield/% 55 | 56 | total |
|---|---|---|---|---|---|---|
| 1 | 4:1 | — | 2:1 | 16 | 0 | 16 |
| 2 | 2.5:1 | — | 2:1 | 7 | 6 | 13 |
| 3 | — | 3:1 | 1:0 | 11 | 2 | 13 |
| 4 | — | 2:1 | 1:0 | 6 | 2 | 8 |
| 5 | — | 1:1 | 1:0 | 5 | 2 | 7 |

Example 5

The type of Ln (OTf)$_3$ employed as the catalyst in Example 3 was changed, and the other conditions were in conformity to Example 1 to carry out the synthesis reaction.

The results are shown in Table 2. According to Table 2, it was found that the synthetic intermediate of isodesmosine and the synthetic intermediate of desmosine were also obtained when various types of Ln(OTf)$_3$ were employed.

TABLE 2

Effects of Ln(OTf)₃.

| entry | Ln(OTf)₃ | yield/% 55 | 56 | total |
|---|---|---|---|---|
| 1 | Pr | 30 | 6 | 36 |
| 2 | La | 21 | 7 | 28 |
| 3 | Nd | 18 | 6 | 24 |
| 4 | Sc | 6[a] | 4[a] | 10 |
| 5 | Y | 12 | 8 | 20 |
| 6 | Gd | 11 | 5 | 16 |
| 7 | Dy | 12 | 8 | 20 |
| 8 | Er | 15[a] | 2[a] | 17 |
| 9 | Yb | 16[a] | 1[a] | 17 |

[a]Determined by $^1$H-NMR.

Example 6

The loading composition ratio between the compound 5' and the compound 54 and the reaction temperature in Example 3 for obtaining the compounds 55 and 56 from the compound 5' and the compound 54 were changed, and the other conditions were in conformity to Example 1 to carry out the synthesis reaction.

The results are shown in Table 3. According to Table 3, it was found that the synthetic intermediate of isodesmosine was able to be selectively obtained by employing the reaction temperature of 80 degrees C. or 100 degrees C. On the other hand, the synthetic intermediate of desmosine and the synthetic intermediate of isodesmosine were able to be obtained at the room temperature or at 40 degrees C.

TABLE 3

| entry | 54/mg (μmol) | 5'/mg (μmol) | ratio (54/5') | temp./° C. | addition | 55/mg | 56/mg | yield/% 55 | 56 | total |
|---|---|---|---|---|---|---|---|---|---|---|
| 1 | 85.6 (213) | 18.0 (63.3) | 4:1 | 40 | — | 19.1 | 4.2 | 24 | 6 | 30 |
| 2 | 62.2 (155) | 13.1 (38.6) | 4:1 | 80 | — | 18.5 | — | 32 | — | 32 |
| 3 | 62.1 (155) | 13.1 (38.7) | 4:1 | 80 | — | 13.1 | — | 23 | — | 23 |
| 4 | 65.1 (162) | 13.7 (40.5) | 4:1 | 100 | — | 8.3 | — | 14 | — | 14 |
| 5 | 48.5 (121) | 10.2 (30.2) | 4:1 | 100 | — | 6.9 | — | 15 | — | 15 |

Example 7

In this example, a labeled isodesmosine and a labeled desmosine, in which nitrogen atom and carbon atom that constitutes pyridine ring were isotopic-labeled, were synthesized.

The synthetic procedure for [(6)-$^{13}$C]—N,N-Bis[(1,1-dimethylethoxy)carbonyl]-6-oxo-1,1-dimethylethyl ester (compound 24) is shown in Scheme 7.

Scheme 7

[Chem. (54)]

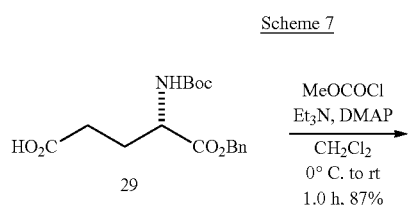

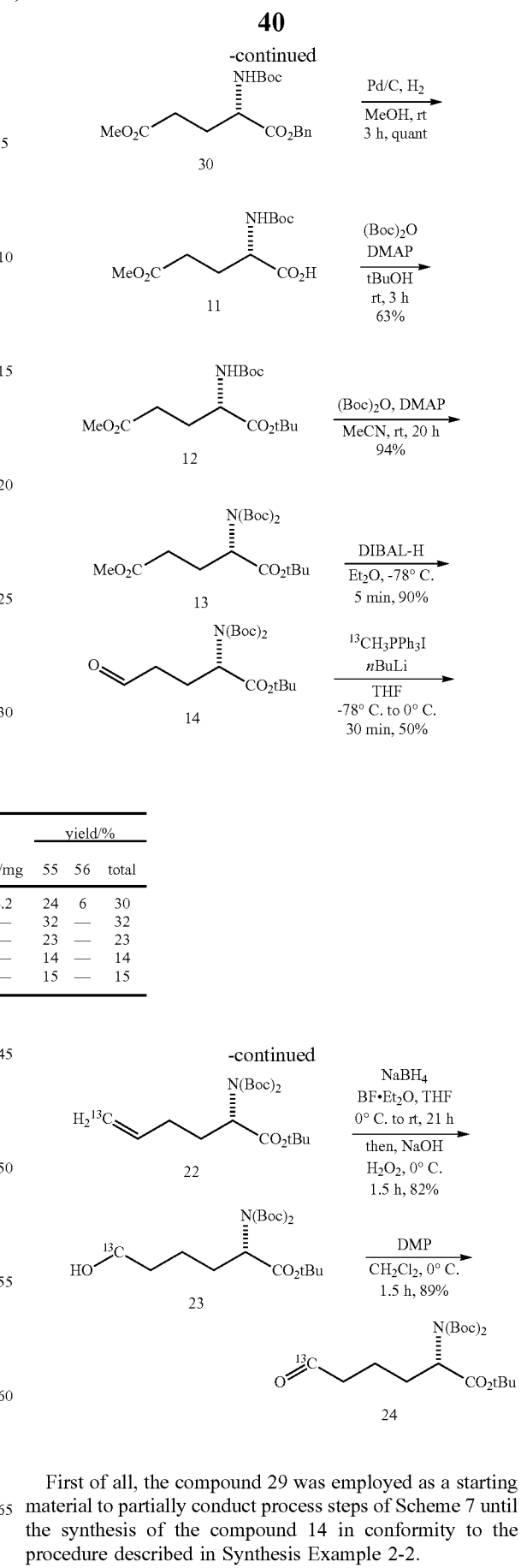

First of all, the compound 29 was employed as a starting material to partially conduct process steps of Scheme 7 until the synthesis of the compound 14 in conformity to the procedure described in Synthesis Example 2-2.

Synthesis of [(6)-$^{13}$C]-1-tert-butyl-2-[bis-(tert-butoxycarbonyl)-amino]-5-hexenoate (Compound 22)

The compound 22 was synthesized as shown in the following formula.

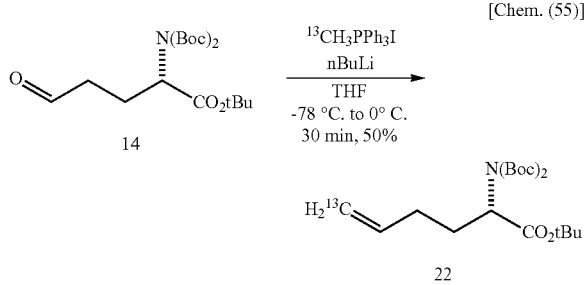

[Chem. (55)]

n-BuLi (1.1 equivalent) was added to a THF (13 mL) solution of $^{13}$CH$_3$PPh$_3$I (1.2 equivalent) at −78 degrees C. Afterwards, it was stirred at 0 degree C. for 1.0 hour. It was cooled again back to −78 degrees C., and then THF (4.9 mL) of the compound 14 (417.2 mg) was added to the reaction solution. It was warmed to 0 degree C., and was stirred for 0.5 hour. Then, after the reaction was stopped with a saturated NH$_4$Cl aqueous solution, the extractions were made for three times in EtOAc. The organic layer was dried with Na$_2$SO$_4$, and then was purified through the silica gel chromatography (hexane/EtOAc=18/1) to obtain 206.1 mg of the compound 22 (50% yield) that was a colorless oily material.

Synthesis of [(6)-$^{13}$C]-tert-Butyl-2-(S)-[bis-(tert-butoxycarbonyl)-amino]-6-hydroxyhexanoate (Compound 23)

The compound 23 was synthesized as shown in the following formula.

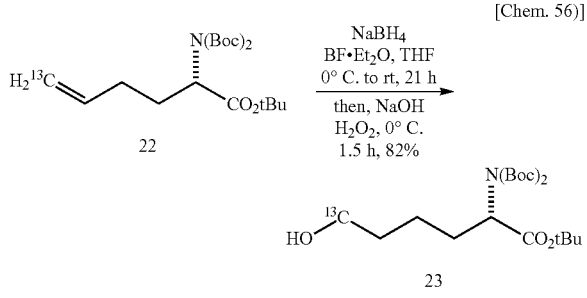

[Chem. 56)]

A THF (2.37 mL) solution of the compound 22 (192.4 mg) was cooled to 0 degree C., and then NaBH$_4$ (1.3 equivalent) was added thereto. After being stirred for 10 minutes, BF$_3$·Et$_2$O (1.3 equivalent) was further added, and was stirred at the room temperature for 21 hours. Then, it was cooled to 0 degree C. again, and after that, 1M NaOH (1.5 equivalent) and 30% H$_2$O$_2$ (0.62 mL) were sequentially added. After the mixture was diluted with water, extractions were made for three times in EtOAc. After being dried with Na$_2$SO$_4$, purification was made through the silica gel chromatography (hexane/EtOAc=5/1) to obtain 201.3 mg of the compound 23 (82% yield) that was a white crystal.

Synthesis of [(6)-$^{13}$C]—N,N-Bis[(1,1-dimethylethoxy)carbonyl]-6-oxo-1,1-dimethylethyl ester (Compound 24)

The compound 24 was synthesized as shown in the following formula.

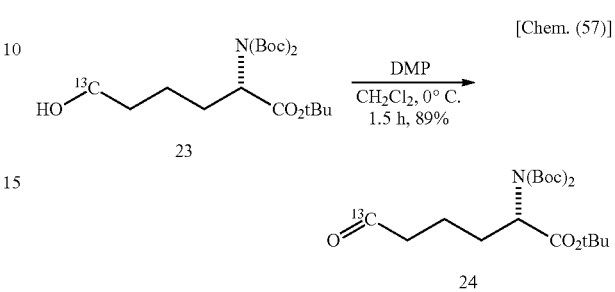

[Chem. (57)]

A CH$_2$Cl$_2$ (2.52 mL) solution of the compound 23 (84.5 mg) was cooled to 0 degree C., and then DMP (1.5 equivalent) was added thereto. Then, after being stirred for 1.5 hour, a solution of NaHCO$_3$/Na$_2$S$_2$O$_3$=1:1 was added to stop the reaction. Next, extractions were made for three times with EtOAc, and then it was dried with Na$_2$SO$_4$. Then, purification was made through the silica gel chromatography (hexane/EtOAc=8/1) to obtain 74.5 mg of the compound 24 (89% yield) as a white crystal.

Next, the synthetic procedure for 5-(S)-(tert-Butoxycarbonyl)-5-[(tert-butoxycarbonyl)-amino]-pentyl-amine-$^{15}$N hydrochloride (Compound 42) is shown in Scheme 8.

Scheme 8

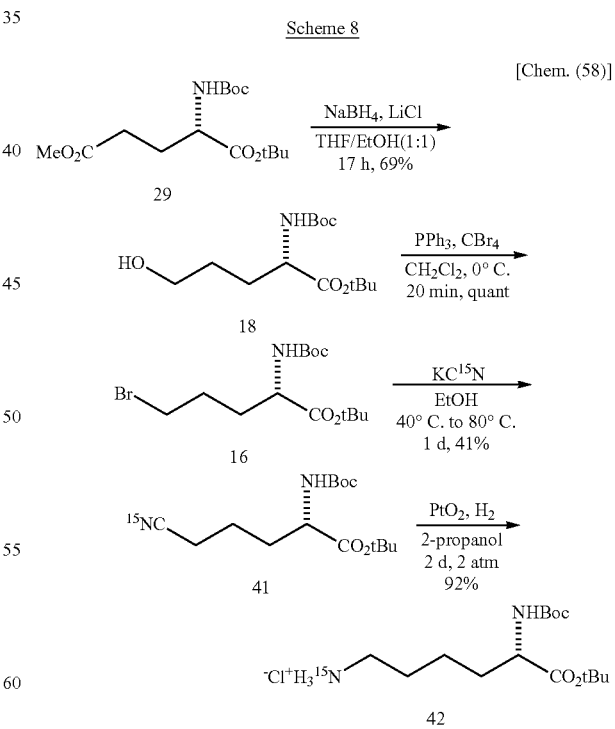

[Chem. (58)]

First of all, the compound 29 was employed as a starting material to partially conduct process steps of Scheme 8 until the synthesis of the compound 16 in conformity to the procedure described in Synthesis Example 3-2.

Synthesis of 5-(cyano-$^{15}$N)-2-[[(1,1-dimethylethoxy)carbonyl]amino]-1,1-dimethylethyl ester (Compound 41)

The compound 41 was synthesized as shown in the following formula.

[Chem. (59)]

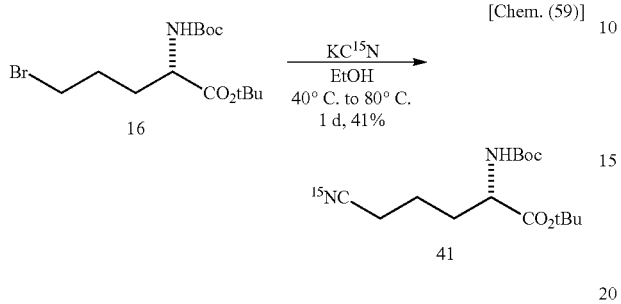

EtOH/H$_2$O (9:1) (2.08 mL) solution of KC$^{15}$N (1.4 equivalent) was added to EtOH (7.07 mL) solution of the compound 16 (117.1 mg). The temperature was gradually elevated from 40 degrees C. to 80 degrees C., and the mixture was stirred for one day. Afterwards, a solid material was removed by a filtration, and then extractions were made twice with CH$_2$Cl$_2$, and it was dried with Na$_2$SO$_4$. Purification was made through the silica gel chromatography (hexane/EtOAc=10/1) to obtain 41.1 mg of the compound 41 (41% yield) that was a colorless oily material.

Synthesis of 5-(S)-(tert-Butoxycarbonyl)-5-[(tert-butoxycarbonyl)-amino]-pentyl-amine-$^{15}$N hydrochloride (Compound 42)

The compound 42 was synthesized as shown in the following formula.

[Chem. (60)]

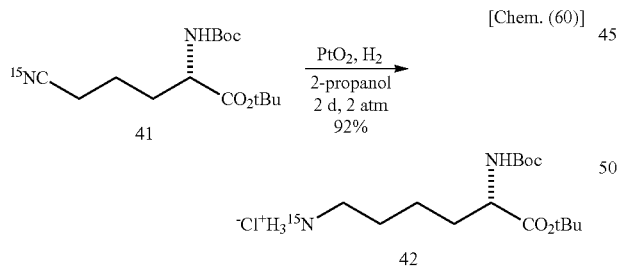

HCl solution (73.8 µL) and PtO$_2$ (0.1 equivalent) were sequentially added to 2-propanol (1.67 mL) solution of the compound 41 (19.5 mg), and it was stirred in the hydrogen atmosphere at 2 atom for two days. Celite filtration of the reaction solution was conducted to remove a solid material, and then concentration under the reduced pressure was carried out to obtain 20.8 mg of the compound 42 (92% yield) as a yellow oily material.

The compound 24 and the compound 42, which were obtained as described above, were employed to synthesize the isotopic-labeled marker of isodesmosine.

Synthesis of 2-{4'-(tert-butoxycarbonyl)-4'-(S)-[bis-(tert-butoxycarbonyl)-amino]-butyl}-3,5-bis-{3'-(tert-butoxycarbonyl)-3'-(S)-[bis-(tert-butoxycarbonyl)-amino]-propyl}-1-{5'-(tert-butoxcarbonyl)-5'-(S)-[bis-(tert-butoxycarbonyl)-amino]-pentyl}-pyridinium-$^{13}$C (2), $^{13}$C (4), $^{13}$C (6), $^{15}$N (1) (Compound 43)

The compound 43 was synthesized as shown in the following formula.

[Chem. (61)]

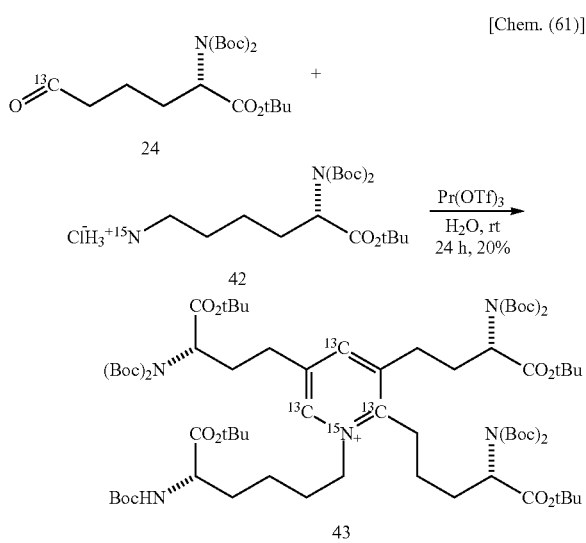

The compound 42 (14.8 mg) was added to the compound 24 (70.1 mg), and then distilled water (2.9 mL) and Pr(OTf)$_3$ (0.5 equivalent) were sequentially added. After being stirred for 24 hours at the room temperature, extractions were made for three times with EtOAc, and then it was dried with Na$_2$SO$_4$. Purification was made through the neutral silica gel chromatography (hexane/EtOAc=1/1, EtOAc, CH$_2$Cl$_2$/methanol=10:1) to obtain 13.2 mg of the compound 43 (20% yield) as a yellow oily material.

Synthesis of 2-(4'-(S)-amino-4'-carboxy-butyl)-1-(5"-(S)-amino-5"-carboxy-pentyl)-3,5-bis-(3'''-(S)-amino-3'''-carboxy-propyl)-pyridinium-$^{13}$C (2), $^{13}$C (4), $^{13}$C (6), $^{15}$N (1), Isodesmosine-$^{13}$C$_3$, $^{15}$N$_1$ (Compound 44)

The compound 44, namely isotopic-labeled marker of isodesmosine, was synthesized as shown in the following formula.

[Chem. (62)]

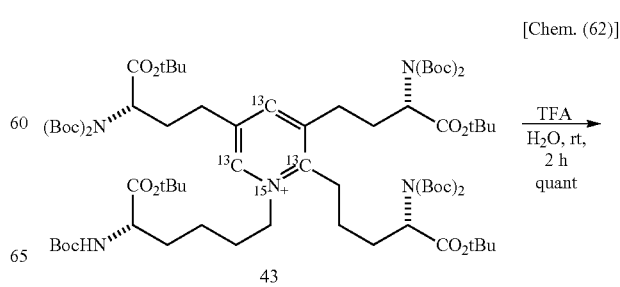

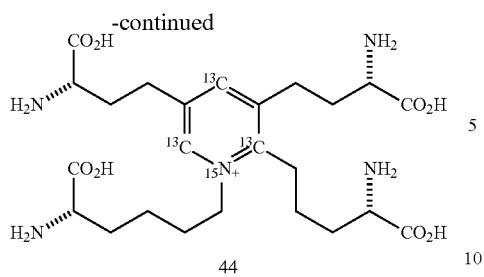

44

A TFA/H$_2$O solution (95:1) (1.33 mL) was add to the compound 43 (8.7 mg), and it was stirred at the room temperature for 2 hours. Afterwards, purification was made through the reversed-phase silica gel chromatography (distilled water, containing 0.1% TFA) to obtain 4.8 mg of the compound 44 (100% yield) as a yellow oily material.

In the present specification, the following abbreviations were employed.
Me: methyl
Et: ethyl
Bu: butyl
Ph: phenyl
Ac: acetyl
rt: room temperature
h: hour
d: day This patent application claims priority on the basis of the Japanese Patent Application No. 2013-018473 filed Feb. 1, 2013, the entire disclosures of which are hereby incorporated by reference.

The invention claimed is:

1. A process for preparing a compound represented by the following formula (I) or a salt thereof:

(I)

[Structure of formula (I)]

wherein, in the formula (I), one of $R^1$ and $R^2$ is —CH$_2$CH$_2$CH$_2$CH(NH$_2$)COOH group, and the other is hydrogen atom and one, or two or more of hydrogen atom, one, or two or more of carbon atom, or one, or two or more of nitrogen atom may be substituted with their isotope, the process comprising:
reacting a compound represented by the following formula (XII) or a salt thereof with a compound represented by the following formula (XIII) in the presence of a compound represented by the following formula (XIV), to create a compound represented by the following formula (XV) or a salt thereof:

(XII)

[Structure of formula (XII)]

wherein, in the formula (XII), $X^1$ is an amino group that may be protected, and $Y^1$ is a carboxylic group that may be protected, and one, or two or more of hydrogen atom, one, or two or more of carbon atom, or one, or two or more of nitrogen atom may be substituted with their isotope;

(XIII)

[Structure of formula (XIII)]

wherein, in the formula (XIII), $X^2$ is an amino group that may be protected, and $Y^2$ is a carboxylic group that may be protected, and one, or two or more of hydrogen atom, one, or two or more of carbon atom, or one, or two or more of nitrogen atom may be substituted with their isotope;

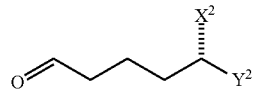

wherein, in formula (XIV), M is a trivalent metallic atom, and Tf is trifluoromethyl sulphonyl group;

(XV)

[Structure of formula (XV)]

wherein, in the formula (XV), $X^1$ and $Y^1$ are identical to $X^1$ and $Y^1$ in the formula (XII), respectively, $X^2$ and $Y^2$ are identical to $X^2$ and $Y^2$ in the formula (XIII) respectively, and one of $R^{17}$ and $R^{18}$ is a —CH$_2$CH$_2$CH$_2$CHX$^3$Y$^3$ group, and the other is hydrogen atom, wherein $X^3$ and $Y^3$ are identical to $X^2$ and $Y^2$ in the formula (XIII), respectively, and wherein, in the formula (XV), one, or two or more of hydrogen atom, one, or two or more of carbon atom, or one, or two or more of nitrogen atom may be substituted with their isotope;

wherein, when at least one of $X^1$, $Y^1$ in the general formula (XII) or $X^2$ and $Y^2$ in the formula (XIII) is a protected group, the process further comprises converting the compound represented by the general formula (XV) or a salt thereof into the compound represented by the general formula (I) or a salt thereof.

2. The process according to claim 1, wherein at least one of $X^1$, $Y^1$ in the formula (XII) and $X^2$ and $Y^2$ in the formula (XIII) is a protected group, and
the process further comprises converting the compound represented by the formula (XV) or a salt thereof into the compound represented by the formula (I) or a salt thereof.

3. The process according to claim 2, wherein the compound represented by the formula (XII) or a salt thereof is a compound represented by the following formula (II) or a salt thereof, and the compound represented by the formula (XIII) is a compound represented by the following formula (III),

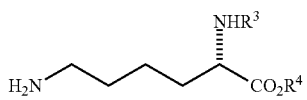 (II)

wherein, in the formula (II), $R^3$ is tert-butyloxycarbonyl group or benzyloxycarbonyl group, $R^4$ is tert-butyl group, benzyl group, methyl group or ethyl group, and one, or two or more of hydrogen atom, one, or two or more of carbon atom, or one, or two or more of nitrogen atom may be substituted with their isotope;

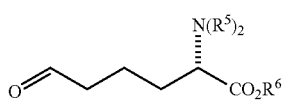 (III)

wherein, in the formula (III), each of $R^5$ is independently tert-butyloxycarbonyl group or benzyloxycarbonyl group, $R^6$ is tert-butyl group, benzyl group, methyl group or ethyl group, and one, or two or more of hydrogen atom, one, or two or more of carbon atom, or one, or two or more of nitrogen atom may be substituted with their isotope.

4. The process according to claim 3, further comprising converting a compound represented by the formula (VI) or a salt thereof into the compound represented by the formula (II) or a salt thereof

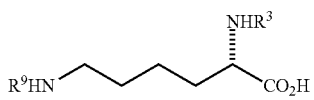 (VI)

wherein, in the formula (VI), $R^3$ is identical to $R^3$ in the above-described formula (II), $R^9$ is tert-butyloxycarbonyl group or benzyloxycarbonyl group, and is a group that is different from $R^3$.

5. The process according to claim 1, wherein water is selected as a reaction solvent in the creating a compound represented by the formula (XV), and a reaction temperature is selected to be equal to or higher than 70 degrees C. and equal to or lower than 100 degrees C.

6. The process according to claim 2, wherein water is selected as a reaction solvent in the creating a compound represented by the formula (XV), and a reaction temperature is selected to be equal to or higher than 70 degrees C. and equal to or lower than 100 degrees C.

7. The process according to claim 3, wherein water is selected as a reaction solvent in the creating a compound represented by the formula (XV), and a reaction temperature is selected to be equal to or higher than 70 degrees C. and equal to or lower than 100 degrees C.

8. The process according to claim 4, wherein water is selected as a reaction solvent in the creating a compound represented by the formula (XV), and a reaction temperature is selected to be equal to or higher than 70 degrees C. and equal to or lower than 100 degrees C.

* * * * *